(12) United States Patent
Huber et al.

(10) Patent No.: US 7,223,907 B2
(45) Date of Patent: May 29, 2007

(54) COTTON EVENT MON15985 AND COMPOSITIONS AND METHODS FOR DETECTION THEREOF

(75) Inventors: Scott A Huber, Creve Coeur, MO (US); James K Roberts, Chesterfield, MO (US); Zachary W Shappley, Collierville, TN (US); Sean Doherty, Richmond Heights, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 10/480,223

(22) PCT Filed: Jun. 5, 2002

(86) PCT No.: PCT/US02/17853

§ 371 (c)(1),
(2), (4) Date: Jun. 7, 2004

(87) PCT Pub. No.: WO02/100163

PCT Pub. Date: Dec. 19, 2002

(65) Prior Publication Data

US 2004/0250317 A1    Dec. 9, 2004

Related U.S. Application Data

(60) Provisional application No. 60/297,406, filed on Jun. 11, 2001.

(51) Int. Cl.
```
A01H 1/00      (2006.01)
A01H 5/00      (2006.01)
A01H 5/10      (2006.01)
C12N 15/82     (2006.01)
```
(52) U.S. Cl. .................. 800/302; 800/267; 800/314
(58) Field of Classification Search ................ 800/314, 800/302, 267, 298
See application file for complete search history.

(56) References Cited

FOREIGN PATENT DOCUMENTS

| WO | WO 99/23232 | 5/1999 |
|---|---|---|
| WO | WO 00/26371 | * 5/2000 |
| WO | WO 00/32800 | 6/2000 |

OTHER PUBLICATIONS

Wilson et al 1994, Crop Science 34: 38-41.*
Dow Agrosciences LLC "Agronomic assessment and seed increase of GM cotton expressing insecticidal genes from Bacillus thuringiensis" Application for License DIR 040/2003 Nov. 2003, p. 28 at Appendix 2.*
J.J. Adamczyk et al., "Evaluation of Bollgard II (cv. DP50BII) in the Mississippi Delta: Field Efficacy Against Various Lepidoptera While Profiling Season-Long Expression of Cry1Ac and Cry2Ab", *Proceedings of the Beltwide Cotton Conference*, 2:835-837 (2001).
D.S. Akin et al., "Field Efficacy of Cotton Expressing Two Insecticidal Proteins of Bacillus Thuringiensis", *Proceedings of the Beltwide Cotton Conference*, 2:1041-1043 (2001).
J.W. Norman et al., "Performance of Bollgard II Cotton Against Lepidopterous Pests in the Lower Rio Grande Valley of Texas", *Proceedings of the Beltwide Conference*, 2:833-835 (2001).
R.E. Jackson et al., "Efficacy of Bollgard and Bollgard II Cottons Against Bollworm, Helicoverpa Zea (Boddie) in Field and Greenhouse Studies", *Proceedings of the Beltwide Conference*, 2:815-819, (2001).
S.D. Stewart et al., "Impact of Bt Cottons Expressing One or Two Insecticidal Proteins of Bacillus Thuringiensis Berliner on Growth and Survival of Noctuid (Lepidoptera) Larvae", *Journal of Economic Entomology*, 94(3):752-760 (2001).
*Federal Register*, 66(55):15867-15868 (2001).
Aphis Petition No. 00-342-01P, CBI Deleted Version, (2000).
P. Windels et al., "Development of a Line Specific GMO Detection Method: A Case Study", *Mededelingen Van De Faculteit Landbouwwetenschappen Universiteit Gent*, 64(5B):459-462 (1999).

* cited by examiner

*Primary Examiner*—David H Kruse
(74) *Attorney, Agent, or Firm*—Timothy K. Ball, Esq.; Howrey, LLP

(57) ABSTRACT

The present invention provides cotton plants, cotton tissues, and cotton seeds that include the MON15985 event, which confers resistance to Lepidopteran insect damage. Also provided are assays for detecting the presence of the MON15985 event based on the DNA sequence of the recombinant construct inserted into the cotton genome that resulted in the MON15985 event and/or the genomic sequences flanking the insertion site.

12 Claims, 1 Drawing Sheet

SEQUENCE LISTING

<160> NUMBER OF SEQ ID NOS: 36

<210> SEQ ID NO 1
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: sequence comprising a junction between insert
      DNA and cotton chromosome

<400> SEQUENCE: 1
gcgtttctgg ttataatata                                                    20

<210> SEQ ID NO 2
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: sequence comprising a junction between insert
      DNA and cotton chromosome

<400> SEQUENCE: 2
cttctctgct aagtgggtca                                                    20

<210> SEQ ID NO 3
<211> LENGTH: 1104
<212> TYPE: DNA
<213> ORGANISM: Artificial Sequence
<220> FEATURE:
<221> NAME/KEY: misc_feature
<222> LOCATION: (1)..(1104)
<223> OTHER INFORMATION: completely synthetic sequence

<400> SEQUENCE: 3
agtacacaaa acaaaagcat catatgctga tttatttatt catagatgga gctcaagtca        60
tagttaaata gcccgatact ttcctcgctc actatgagct attacagcat acattttagt       120
actacatact tattcagtaa aaagccctca aaattgaaga caaggacgg gatccccggg         180 taccgagctc gaattcaggc tctagatct cattattcct ccatcaagag aagctccacg        240
ctgtccacga tgaaggttcc ctcggtttca ccgatctcga tccacacttt gtcggtctca       300
ggaaagtact caagctcctt ggtaacatag ccaactggaa gtggtgtgta gtccctgtaa       360
cctctgttga actcgcaagg gttctcacgt ctgccatctg tgtaggattt ctcctcgtac       420
acggaggcat agtcagcagg aacggaagga gcttcgttgt aacctctgtt acggctagtg       480
taggcacctc cgtactcttc ctgattcaca gtgtagtcgt tgcaagtaac ggtgttgttg       540
ggatagattt cttcctcgac gcagttggag aacttaagct cgtcggtgtt gttctcgatc       600
tcgtggatgg tcacgcaacc ctcaccgtat ccctccttgt aagcggtcac acggagaatg       660
tagcctctac ctggacagac tctaacctct tgggacactt cagcttccca ctcaggcaca       720
accaggacgg aacgctgatt gttctgttcc tccacgtcca catgaccttt cacattccag       780
cagctgaggc cattgttgaa gtcaccgttc ttgatgacgt ttctggcatc gtacaaggag       840
aatgcggtaa agatacgtcc ctcaagttcc tcgaagatgg cagcgttcac accagggatc       900
acggacaact caggcaagta agcctcacga atgctgtgca cacgtttgtc tgcggcgtgg       960
atcatggcga tgttggtgtc ggcttgcaac tgatcatatt gggagttcac gaacaaagca      1020

```
tccacggact ctttggcctc cttgtaaacg atgttagttt cccattcgag tttctcacgt    1080
ttgtccctcc acttcttctc tgct                                          1104

<210> SEQ ID NO 4
<211> LENGTH: 309
<212> TYPE: DNA
<213> ORGANISM: Gossypium hirsutum

<400> SEQUENCE: 4
aagtgggtca gtggggtggc attggttttt aatttcaacg cgttttgtcg catatacttt     60
tatgattggg gtttctcttt ggtgtacatc aatgaccttc cctattgcat tgtctgaatt    120
ttcatctctt aaatcggcta aaaacaact atgaaaaaaa gagtaggcct actcatccgt    180
accggggagg ggggggggaa tggaggaaat agaatagggg actcatttat atatatataa    240
accaagtatg ttattggttg atcgagtggg aaggaattca atgttcaatt ctgggtttga    300
aacttgctt                                                            309

<210> SEQ ID NO 5
<211> LENGTH: 378
<212> TYPE: DNA
<213> ORGANISM: Artificial Sequence
<220> FEATURE:
<221> NAME/KEY: misc_feature
<222> LOCATION: (1)..(378)
<223> OTHER INFORMATION: completely synthetic sequence

<400> SEQUENCE: 5
cccctcaaat gtcaataggt gcgcccctca tctgtcagca ctctgcccct caagtgtcaa     60
ggatcgcgcc cctcatctgt cagtagtcgc gcccctcaag tgtcaatacc gcagggcact    120
tatccccagg cttgtccaca tcatctgtgg gaaactcgcg taaaatcagg cgttttcgcc    180
gatttgcgag gctggccagc tccacgtcgc cggccgaaat cgagcctgcc cctcatctgt    240
caacgccgcg ccgggtgagt cggcccctca agtgtcaacg tccgcccctc atctgtcagt    300
gagggccaag ttttccgcga ggtatccaca acgccggcgg ccgcggtgtc tcgcacacgg    360
cttcgacggc gtttctgg                                                  378

<210> SEQ ID NO 6
<211> LENGTH: 211
<212> TYPE: DNA
<213> ORGANISM: Gossypium hirsutum

<400> SEQUENCE: 6
ttataatata cacatatata atttatcact gtatattctt gcagagaaca atcacgaggc     60
attggcccct ccattttttt aaaaaaaatt tgatctgata gagaaaagaa agaaagaaaa    120
agaagaatat tagtgacctt tcaatggtga aaaatcaaaa aaaaatctca tttaatgata    180
aacaaaatgt caaacagtct gacagctcct g                                   211

<210> SEQ ID NO 7
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: completely synthetic sequence

<400> SEQUENCE: 7
```

```
gccaatgcct cgtgattgtt ctctgc                                              26
```

<210> SEQ ID NO 8
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: completely synthetic sequence

<400> SEQUENCE: 8

```
gatttgcgag gctggccagc tccacg                                              26
```

<210> SEQ ID NO 9
<211> LENGTH: 589
<212> TYPE: DNA
<213> ORGANISM: Artificial Sequence
<220> FEATURE:
<221> NAME/KEY: misc_feature
<222> LOCATION: (1)..(378)
<223> OTHER INFORMATION: MON531 3' insert sequence, completely synthetic
<220> FEATURE:
<221> NAME/KEY: misc_feature
<222> LOCATION: (379)..(589)
<223> OTHER INFORMATION: MON531 3' end Gossypium hirsutum flanking
      sequence

<400> SEQUENCE: 9

```
cccctcaaat gtcaataggt gcgcccctca tctgtcagca ctctgcccct caagtgtcaa        60
ggatcgcgcc cctcatctgt cagtagtcgc gcccctcaag tgtcaatacc gcagggcact       120
tatccccagg cttgtccaca tcatctgtgg gaaactcgcg taaaatcagg cgttttcgcc       180
gatttgcgag gctggccagc tccacgtcgc cggccgaaat cgagcctgcc cctcatctgt       240
caacgccgcg ccgggtgagt cggcccctca agtgtcaacg tccgcccctc atctgtcagt       300
gagggccaag ttttccgcga ggtatccaca acgccggcgg ccgcggtgtc tcgcacacgg       360
cttcgacggc gtttctggtt ataatataca catatataat ttatcactgt atattcttgc       420
agagaacaat cacgaggcat tggcccctcc atttttttaa aaaaaatttg atctgataga       480
gaaaagaaag aaagaaaaag aagaatatta gtgacctttc aatggtgaaa aatcaaaaaa       540
aaatctcatt taatgataaa caaaatgtca acagtctga cagctcctg                    589
```

<210> SEQ ID NO 10
<211> LENGTH: 1411
<212> TYPE: DNA
<213> ORGANISM: Artificial Sequence
<220> FEATURE:
<221> NAME/KEY: misc_feature
<222> LOCATION: (1)..(1104)
<223> OTHER INFORMATION: completely synthetic insert sequence
<220> FEATURE:
<221> NAME/KEY: misc_feature
<222> LOCATION: (1105)..(1411)
<223> OTHER INFORMATION: MON531 5' end Gossypium hirsutum flanking
      sequence

<400> SEQUENCE: 10

```
agtacacaaa acaaaagcat catatgctga tttatttatt catagatgga gctcaagtca        60
tagttaaata gcccgatact ttcctcgctc actatgagct attacagcat acattttagt       120
actacatact tattcagtaa aaagccctca aaattgaaga caaaggacgg gatccccggg       180
taccgagctc gaattcaggc ctctagatct cattattcct ccatcaagag aagctccacg       240
ctgtccacga tgaaggttcc ctcggtttca ccgatctcga tccacacttt gtcggtctca       300
```

-continued

```
ggaaagtact caagctcctt ggtaacatag ccaactggaa gtggtgtgta gtccctgtaa      360
cctctgttga actcgcaagg gttctcacgt ctgccatctg tgtaggattt ctcctcgtac      420
acggaggcat agtcagcagg aacggaagga gcttcgttgt aacctctgtt acggctagtg      480
taggcacctc cgtactcttc ctgattcaca gtgtagtcgt tgcaagtaac ggtgttgttg      540
ggatagattt cttcctcgac gcagttggag aacttaagct cgtcggtgtt gttctcgatc      600
tcgtggatgg tcacgcaacc ctcaccgtat ccctccttgt aagcggtcac acggagaatg      660
tagcctctac ctggacagac tctaacctct tgggacactt cagcttccca ctcaggcaca      720
accaggacgg aacgctgatt gttctgttcc tccacgtcca catgaccttt cacattccag      780
cagctgaggc cattgttgaa gtcaccgttc ttgatgacgt ttctggcatc gtacaaggag      840
aatgcggtaa agatacgtcc ctcaagttcc tcgaagatgg cagcgttcac accagggatc      900
acggacaact caggcaagta agcctcacga atgctgtgca cacgtttgtc tgcggcgtgg      960
atcatggcga tgttggtgtc ggcttgcaac tgatcatatt gggagttcac gaacaaagca     1020
tccacggact ctttggcctc cttgtaaacg atgttagttt cccattcgag tttctcacgt     1080
ttgtccctcc acttcttctc tgctaagtgg gtcagtgggg tggcattggt tttaatttc      1140
aacgcgtttt gtcgcatata cttttatgat tggggtttct ctttggtgta catcaatgac     1200
cttccctatt gcattgtctg aattttcatc tcttaaatcg gctaaaaaac aactatgaaa     1260
aaaagagtag gcctactcat ccgtaccggg gaggggggg ggaatggagg aaatagaata     1320
ggggactcat ttatatatat ataaaccaag tatgttattg gttgatcgag tgggaaggaa     1380
ttcaatgttc aattctgggt ttgaaacttg c                                    1411
```

<210> SEQ ID NO 11
<211> LENGTH: 2267
<212> TYPE: DNA
<213> ORGANISM: Artificial Sequence
<220> FEATURE:
<221> NAME/KEY: misc_feature
<222> LOCATION: (1)..(361)
<223> OTHER INFORMATION: Gossypium hirsutum 5' end genomic DNA sequence
<220> FEATURE:
<221> NAME/KEY: misc_feature
<222> LOCATION: (362)..(750)
<223> OTHER INFORMATION: 5' end chloroplast related DNA sequence
<220> FEATURE:
<221> NAME/KEY: misc_feature
<222> LOCATION: (751)..(1885)
<223> OTHER INFORMATION: 5' end Gossypium hirsutum remnant DNA sequence
<220> FEATURE:
<221> NAME/KEY: misc_feature
<222> LOCATION: (1886)..(2267)
<223> OTHER INFORMATION: 5' end inserted DNA sequence

<400> SEQUENCE: 11

```
cttgtcattg gtgcagacag gttcggggag tatggcctat gggtggtggt agagagaaag       60
taacagcgaa atcttagggt ggtccgagaa atgagattgt taagtcctga tttaatgtgc      120
tgagttcagt tgatggagag gaaaatggca aagatttgag gggagaggat tttgtggatc      180
ctaacattaa acagaatcgt tctactaaaa ggggtaaggg tagtggtgga agagatattt      240
ttaaaaagc taaggtaaaa tctgggcaaa gttttaacgt ggcccagggg aataaaaag      300
ggactatagg gcctagtggt agtcaacagg ccgggcggga agtattcat ttgaaatggg      360
tttattcgta ttaacagcta ctctaggagg aatgttttta tgcggtgcta acgatttaat      420
aactatcttt gtagctccag aatgtttcag tttatgctcc tacctattat ctggatatac      480
```

```
caagaaagat gtacggtcta atgaggctac tacgaaatat ttactcatgg gtggggcaag    540
ctcttctatt ctggttcatg gtttctcttg gctatatggt tcatccgggg gagagatcga    600
gcttcaagaa atagtgaatg gtcttatcaa tacacaaatg tataactccc caggaatttc    660
aattgcgctt atattcatca ctgtaggaat tgggttcaag ctttcccag ccccttctca     720 tcaatggact cctgacgtat acgaaggagt tcttttaggc ttttgcattt tgttgaaaat    780 tcttatttc acaggactt gcttatcata attattgaca gccaactggt gaaaatggtg     840
ccacgagagc tcccatcagc attgatttgg ctagggatag ttctttaagt gctaagtcaa    900
tcatcttgca aattgacaat aaatctcaac aggtttcagc aagtaaggcc tccttcatta    960 tttggttgc ttcttttca ttaatgatgt tgcttgtttg cacctggaaa acatgcaccg     1020
ttcttcatca tgcaccttgg atatggtctt gagtgctctc tgactgcccg tcatctttcg    1080
aattggtgtc tgattgagtg cacccgccta agttcaagat gccggagttt gaatagtata    1140 acggactag ttgtcttgag gctcatatta ctatgttctg tcgatataat catccatggg     1200
cttcgcatcc accattgcaa ggcccaacca cctagcactg tgatgggtcc aaacgcaaag    1260
gtgatccctt taggccaaat ggatggagac gctataagat tggtcaccgc aagaaaagtg    1320
tggatcgata ggccctgtag ttgatgatgg ggatgatcac gatgaccctg cctatcctcc    1380
aagtttcacc ccaactaaca tccaagtgca accagaggtg tacccgcaga gggcaccctat    1440 taccattaga tcgactgcaa gtgtaggtaa tgttggacag ggtagatcag ggtgttcacg    1500
gtgtggtaga ctttactatg gtccttttcg ggcaggcgaa aatgtttgtt ataaatgcgg    1560
cactccagat cattttgtac gagaatgtcc agaggtggct aatcgagaga tcgaatcac    1620 ttacgaaaaa agattattgt tactaagttt tcatgtttta tgccatgcgt agccatgttt    1680
ttaataaagg gttgaagact tgaatgacaa gttagcgtaa agcatttttt ttctttcatg    1740
ttggcacatt tgatgcacta tgtcttcgtc tattttttcaa acatactgtt ggaagaatta    1800
tgattcacgt gttgtttaag atcaaaaagt gcatgcctaa ctaatactta tcagaaacaa    1860
ataatgcaat gagtcatatc tctataaagg gtaatatccg gaaacctcct cggattccat    1920
tgcccagcta tctgtcactt tattgtgaag atagtggaaa aggaaggtgg ctcctacaaa    1980
tgccatcatt gcgataaagg aaaggccatc gttgaagatg cctctgccga cagtggtccc    2040
aaagatggac ccccacccac gaggagcatc gtggaaaaag aagacgttcc aaccacgtct    2100
tcaaagcaag tggattgata tgatatctcc actgacgtaa gggatgacgc acaatcccac    2160
tatccttcgc aagacccttc ctctatataa ggaagttcat ttcatttgga gaggacacgc    2220
tgacaagctg actctagcag atctccatgg tccgtcctgt agaaacc                  2267
```

<210> SEQ ID NO 12
<211> LENGTH: 1360
<212> TYPE: DNA
<213> ORGANISM: Artificial Sequence
<220> FEATURE:
<221> NAME/KEY: misc_feature
<222> LOCATION: (1)..(349)
<223> OTHER INFORMATION: 3' end insert sequence
<220> FEATURE:
<221> NAME/KEY: misc_feature
<222> LOCATION: (350)..(673)
<223> OTHER INFORMATION: 3' end Gossypium hirsutum remnant DNA sequence
<220> FEATURE:
<221> NAME/KEY: misc_feature
<222> LOCATION: (674)..(1360)
<223> OTHER INFORMATION: 3' end Gossypium hirsutum chromosomal sequence

<400> SEQUENCE: 12

```
ccaactaaca tctcgccgct gtactgatag gagctctgat ccccatggga attcccgatc    60
gttcaaacat ttggcaataa agtttcttaa gattgaatcc tgttgccggt cttgcgatga   120
ttatcatata atttctgttg aattacgtta agcatgtaat aattaacatg taatgcatga   180
cgttatttat gagatgggtt tttatgatta gagtcccgca attatacatt taatacgcga   240
tagaaaacaa aatatagcgc gcaaactagg ataaattatc gcgcgcggtg tcatctatgt   300
tactagatcg gggatatccc cggggcggcc gctctagaac tagtggatct gcactgaaat   360
cccatccatt tagcaacctt aaaagtaata aacttaaact aagtgtactc cttatcaaaa   420
cataaaccaa gagatgagga taacagcgtt cggccaaccc caataccacc tataatcaaa   480
gcatgcgatg tcacgaacgt tttcctgacg gcaatcgaca caagaagag attaaaaagg     540
gagaccacta tagaaagaag aaagagaatc ggcaccactg tgaaactaca tttgataacc   600
gtattagcaa ggctccacca ttgataaaaa ctcgacaacc aagaggaact cacttacctt   660
gatcaaagta gggttgttgg tactaaggct caaagcaagg aaaatgtcta aatgagtgag   720
ttgggctttt ttaatttaat taaactgaaa aataagaaag gatgttgcca attttgtgtg   780
gcaaggacgg acaagaggtt tcgacccaac ctagagaaga cattaaaaact gcagaactgg   840
gctcgcttgt tcaggatcgg gctttaaagg agaatggttt gatggaccag aatagagaca   900
aaccaataca ctcagatttt gatcttcctt attctccctc aactattgat tttgttttgg   960
gtaatgatgg tgtagcaggg gatcgggttt taggtgtttt tcaaggcatg actgttactc  1020
attttaatcc gacttgcgat gaccataatg agatggaggc tgtactgaag gatgaagtat  1080
tggatccaaa taggcattcg acatgtttga taaaactctt agttacaaaa ttcttagtaa  1140
acgaatccat aaggttatct ttagatgtta ttttcatcac atctataatt ctttcagcta  1200
ctgcctcttg tatcaagtga tactttcagt cagtatattc gtcttgcagc actgttatca  1260
caatacagtg ttatatcttt ttctatatca ggaatgactt caagatcggt taagaacttt  1320
taaagccata ttgtttcttt cgtagcctca gaagcaacca                        1360

<210> SEQ ID NO 13
<211> LENGTH: 1050
<212> TYPE: DNA
<213> ORGANISM: Gossypium hirsutum

<400> SEQUENCE: 13
cttgtcattg gtgcagacag gttcggggag tatggcctat gggtggtggt agagagaaag    60
taacagcgaa atcttagggt ggtccgagaa atgagattgt taagtcctga tttaatgtgc   120
tgagttcagt tgatggagag gaaaatggca agatttgag gggagaggat tttgtggatc   180
ctaacattaa acagaatcgt tctactaaaa ggggtaaggg tagtggtgga agagatattt   240
ttaaaaagc taaggtaaaa tctgggcaaa gttttaacgt ggcccagggg aataaaaaag   300
ggactatagg gcctagtggt agtcaacagg ccgggcggga agtattcat ttgaaatggg    360
ttgttgttgg tactaaggct caaagcaagg aaaatgtcta aatgagtgag ttgggctttt   420
ttaatttaat taaactgaaa aataagaaag gatgttgcca attttgtgtg gcaaggacgg   480
acaagaggtt tcgacccaac ctagagaaga cattaaaact gcagaactgg gctcgcttgt   540
tcaggatcgg gctttaaagg agaatggttt gatggaccag aatagagaca aaccaataca   600
ctcagatttt gatcttcctt attctccctc aactattgat tttgttttgg gtaatgatgg   660
tgtagcaggg gatcgggttt taggtgtttt tcaaggcatg actgttactc attttaatcc   720
```

```
gacttgcgat gaccataatg agatggaggc tgtactgaag gatgaagtat tggatccaaa      780
taggcattcg acatgtttga taaaactctt agttacaaaa ttcttagtaa acgaatccat      840
aaggttatct ttagatgtta ttttcatcac atctataatt ctttcagcta ctgcctcttg      900
tatcaagtga tactttcagt cagtatattc gtcttgcagc actgttatca caatacagtg      960
ttatatcttt ttctatatca ggaatgactt caagatcggt taagaacttt taaagccata     1020
ttgtttcttt cgtagcctca gaagcaacca                                      1050
```

```
<210> SEQ ID NO 14
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: 5' event end cotton genome sequence flanking
      chloroplast related sequence

<400> SEQUENCE: 14
tgaaatgggt ttattcgtat                                                    20

<210> SEQ ID NO 15
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: 5' end chloroplast related sequence adjacent to
      5' end cotton genome sequence

<400> SEQUENCE: 15
acgaaggagt tcttttaggc                                                    20

<210> SEQ ID NO 16
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: 5' end cotton genomic remnant sequence adjacent
      to 5' end insert sequence

<400> SEQUENCE: 16
atatctctat aaagggtaat                                                    20

<210> SEQ ID NO 17
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: 3' end insert sequence at NOS3' adjacent to 3'
      end cotton genomic

<400> SEQUENCE: 17
ctagtggatc tgcactgaaa                                                    20

<210> SEQ ID NO 18
<211> LENGTH: 20
<212> TYPE: DNA
<213> ORGANISM: Artificial Sequence
<220> FEATURE:
<221> NAME/KEY: misc_feature
```

```
<222> LOCATION: (1)..(20)
<223> OTHER INFORMATION: 3' end cotton genomic remnant sequence adjacent
      to 3' end Gossypium hirsutum chromosome sequence

<400> SEQUENCE: 18
tcaaagtagg gttgttggta                                                20

<210> SEQ ID NO 19
<211> LENGTH: 361
<212> TYPE: DNA
<213> ORGANISM: Gossypium hirsutum

<400> SEQUENCE: 19
cttgtcattg gtgcagacag gttcggggag tatggcctat gggtggtggt agagagaaag     60
taacagcgaa atcttagggt ggtccgagaa atgagattgt taagtcctga tttaatgtgc    120
tgagttcagt tgatggagag gaaaatggca agatttgag gggagaggat tttgtggatc     180
ctaacattaa acagaatcgt tctactaaaa ggggtaaggg tagtggtgga agagatattt    240 ttaaaaagc taaggtaaaa tctgggcaaa gttttaacgt ggcccagggg aataaaaaag    300
ggactatagg gcctagtggt agtcaacagg ccgggcggga agtattcat ttgaaatggg     360 t                                                                   361

<210> SEQ ID NO 20
<211> LENGTH: 389
<212> TYPE: DNA
<213> ORGANISM: unidentified plant
<220> FEATURE:
<221> NAME/KEY: misc_feature
<222> LOCATION: (1)..(389)
<223> OTHER INFORMATION: chloroplast related DNA sequence adjacent to 5'
      flanking Gossypium hirsutum sequence

<400> SEQUENCE: 20
ttattcgtat taacagctac tctaggagga atgtttttat gcggtgctaa cgatttaata     60
actatctttg tagctccaga atgtttcagt ttatgctcct acctattatc tggatatacc    120
aagaaagatg tacggtctaa tgaggctact acgaaatatt tactcatggg tggggcaagc    180
tcttctattc tggttcatgg tttctcttgg ctatatggtt catccggggg agagatcgag    240
cttcaagaaa tagtgaatgg tcttatcaat acacaaatgt ataactcccc aggaatttca    300
attgcgctta tattcatcac tgtaggaatt gggttcaagc tttccccagc cccttctcat    360
caatggactc ctgacgtata cgaaggagt                                      389

<210> SEQ ID NO 21
<211> LENGTH: 1135
<212> TYPE: DNA
<213> ORGANISM: Gossypium hirsutum

<400> SEQUENCE: 21
tcttttaggc ttttgcattt tgttgaaaat tcttattttc acaggacttt gcttatcata     60
attattgaca gccaactggt gaaaatggtg ccacgagagc tcccatcagc attgatttgg    120
ctagggatag ttcttaagt gctaagtcaa tcatcttgca aattgacaat aaatctcaac    180
aggtttcagc aagtaaggcc tccttcatta ttttggttgc ttcttttca ttaatgatgt    240 tgcttgtttg cacctggaaa acatgcaccg ttcttcatca tgcaccttgg atatggtctt    300
gagtgctctc tgactgcccg tcatctttcg aattggtgtc tgattgagtg caccgccta    360 agttcaagat gccggagttt gaatagtata acgggactag ttgtcttgag gctcatatta    420
```

```
ctatgttctg tcgatataat catccatggg cttcgcatcc accattgcaa ggcccaacca      480
cctagcactg tgatgggtcc aaacgcaaag gtgatccctt taggccaaat ggatggagac      540
gctataagat tggtcaccgc aagaaaagtg tggatcgata ggccctgtag ttgatgatgg      600
ggatgatcac gatgaccctg cctatcctcc aagtttcacc ccaactaaca tccaagtgca      660
accagaggtg tacccgcaga gggcacctat taccattaga tcgactgcaa gtgtaggtaa      720
tgttggacag ggtagatcag ggtgttcacg gtgtggtaga ctttactatg gtccttttcg      780
ggcaggcgaa aatgtttgtt ataaatgcgg cactccagat cattttgtac gagaatgtcc      840
agaggtggct aatcgagaga atcgaatcac ttacgaaaaa agattattgt tactaagttt      900
tcatgtttta tgccatgcgt agccatgttt ttaataaagg gttgaagact tgaatgacaa      960
gttagcgtaa agcattttt ttctttcatg ttggcacatt tgatgcacta tgtcttcgtc     1020 tattttcaa acatactgtt ggaagaatta tgattcacgt gttgtttaag atcaaaaagt     1080
gcatgcctaa ctaatactta tcagaaacaa ataatgcaat gagtcatatc tctat         1135
```

<210> SEQ ID NO 22
<211> LENGTH: 382
<212> TYPE: DNA
<213> ORGANISM: Artificial Sequence
<220> FEATURE:
<221> NAME/KEY: misc_feature
<222> LOCATION: (1)..(382)
<223> OTHER INFORMATION: completely synthesized 5' end insert sequence
      corresponding to enhanced 35S promoter sequence

<400> SEQUENCE: 22

```
aaagggtaat atccggaaac ctcctcggat tccattgccc agctatctgt cactttattg       60
tgaagatagt ggaaaggaa ggtggctcct acaaatgcca tcattgcgat aaaggaaagg      120
ccatcgttga agatgcctct gccgacagtg gtcccaaaga tggaccccca cccacgagga      180
gcatcgtgga aaagaagac gttccaacca cgtcttcaaa gcaagtggat tgatatgata      240
tctccactga cgtaagggat gacgcacaat cccactatcc ttcgcaagac ccttcctcta      300
tataaggaag ttcatttcat ttggagagga cacgctgaca agctgactct agcagatctc      360
catggtccgt cctgtagaaa cc                                              382
```

<210> SEQ ID NO 23
<211> LENGTH: 349
<212> TYPE: DNA
<213> ORGANISM: Agrobacterium tumefaciens

<400> SEQUENCE: 23

```
ccaactaaca tctcgccgct gtactgatag gagctctgat ccccatggga attcccgatc       60
gttcaaacat ttggcaataa agtttcttaa gattgaatcc tgttgccggt cttgcgatga      120
ttatcatata atttctgttg aattacgtta agcatgtaat aattaacatg taatgcatga      180
cgttatttat gagatgggtt tttatgatta gagtcccgca attatacatt taatacgcga      240
tagaaaacaa aatatagcgc gcaaactagg ataaattatc gcgcgcggtg tcatctatgt      300
tactagatcg gggatatccc cggggcggcc gctctagaac tagtggatc                 349
```

<210> SEQ ID NO 24
<211> LENGTH: 323
<212> TYPE: DNA
<213> ORGANISM: Gossypium hirsutum

<400> SEQUENCE: 24

```
tgcactgaaa tcccatccat ttagcaacct taaaagtaat aaacttaaac taagtgtact    60
ccttatcaaa acataaacca agagatgagg ataacagcgt tcggccaacc ccaataccac   120
ctataatcaa agcatgcgat gtcacgaacg ttttcctgac ggcaatcgac acaaagaaga   180
gattaaaaag ggagaccact atagaaagaa gaaagagaat cggcaccact gtgaaactac   240
atttgataac cgtattagca aggctccacc attgataaaa actcgacaac caagaggaac   300
tcacttacct tgatcaaagt agg                                          323
```

<210> SEQ ID NO 25
<211> LENGTH: 688
<212> TYPE: DNA
<213> ORGANISM: Gossypium hirsutum

<400> SEQUENCE: 25

```
gttgttggta ctaaggctca aagcaaggaa aatgtctaaa tgagtgagtt gggctttttt    60
aatttaatta aactgaaaaa taagaaagga tgttgccaat tttgtgtggc aaggacggac   120
aagaggtttc gacccaacct agagaagaca ttaaaactgc agaactgggc tcgcttgttc   180
aggatcgggc tttaaaggag aatggtttga tggaccagaa tagagacaaa ccaatacact   240
cagattttga tcttccttat tctccctcaa ctattgattt tgttttgggt aatgatggtg   300
tagcagggga tcgggtttta ggtgtttttc aaggcatgac tgttactcat tttaatccga   360
cttgcgatga ccataatgag atggaggctg tactgaagga tgaagtattg gatccaaata   420
ggcattcgac atgtttgata aaactcttag ttacaaaatt cttagtaaac gaatccataa   480
ggttatcttt agatgttatt ttcatcacat ctataattct ttcagctact gcctcttgta   540
tcaagtgata ctttcagtca gtatattcgt cttgcagcac tgttatcaca atacagtgtt   600
atatcttttt ctatatcagg aatgacttca agatcggtta agaacttttt aagccatatt   660
gtttctttcg tagcctcaga agcaacca                                     688
```

<210> SEQ ID NO 26
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: completely synthesized

<400> SEQUENCE: 26

```
gtggcccagg ggaataaaa                                                19
```

<210> SEQ ID NO 27
<211> LENGTH: 23
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: completely synthesized

<400> SEQUENCE: 27

```
ttgcgaagga tagtgggatt gtg                                           23
```

<210> SEQ ID NO 28
<211> LENGTH: 24
<212> TYPE: DNA
<213> ORGANISM: Artificial Sequence
<220> FEATURE:
<221> NAME/KEY: misc_feature

```
<222> LOCATION: (1)..(24)
<223> OTHER INFORMATION: completely synthesized

<400> SEQUENCE: 28
taatacgcga tagaaaacaa aata                                              24

<210> SEQ ID NO 29
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: completely synthesized

<400> SEQUENCE: 29 ctaaacccg atccctgct acac                                                24

<210> SEQ ID NO 30
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: completely synthesized

<400> SEQUENCE: 30
gactgaatgc ccacaggccg tcgagtt                                           27

<210> SEQ ID NO 31
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: completely synthesized

<400> SEQUENCE: 31
cctgaactct ggcacccagt tcgacc                                            26

<210> SEQ ID NO 32
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: completely synthesized

<400> SEQUENCE: 32
ggtttctaca ggacggacca tggagatctg c                                      31

<210> SEQ ID NO 33
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: completely synthesized

<400> SEQUENCE: 33
ccaactaaca tctcgccgct gtactgatag g                                      31

<210> SEQ ID NO 34
```

-continued

```
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: completely synthesized

<400> SEQUENCE: 34
tggttgcttc tgaggctac                                              19

<210> SEQ ID NO 35
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: completely synthesized

<400> SEQUENCE: 35
cttgtcattg gtgcagacag gttc                                        24

<210> SEQ ID NO 36
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: completely synthesized

<400> SEQUENCE: 36
gcttcaccat ctctccaatc cacg                                        24
```

COTTON EVENT MON15985 AND COMPOSITIONS AND METHODS FOR DETECTION THEREOF

Figure 1:
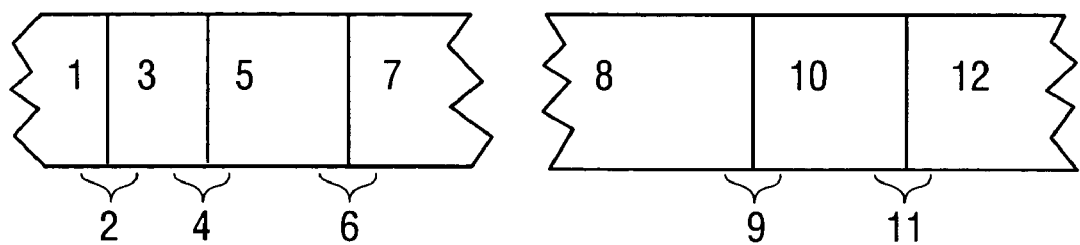

This application is a §371 U.S. National phase application of International Application No. PCT/US02/17853 filed Jun. 5, 2002, and claims benefit of priority to U.S. Provisional Application No. 60/297,406, filed Jun. 11, 2001.

FIELD OF THE INVENTION

This invention is in the field of plant molecular biology, and in particular to plant insect protection and plant breeding, and is directed to a novel transformation event of cotton plants, Gossypium hirsutum, comprising a polynucleotide sequence inserted into a specific site within the genome of a cotton cell, said sequence encoding a Cry2Ab lepidopteran insect inhibitory protein. Additionally, the invention is related to cotton plants derived from that transformation event and to assays for detecting the presence of the event in a sample.

BACKGROUND OF THE INVENTION

This invention relates to a previously commercialized Lepidopteran resistant cotton plant event, known as MON531, expressing a chimeric form of a Cry1A insect inhibitory protein. Cotton plants are susceptible to insect infestation in all areas of the world in which the plants are cultivated. Recombinant DNA technology has been applied to cells of the cotton plant for about a decade, and cotton plants which exhibit improved characteristics as a result of the insertion of heterologous DNA sequences have been produced using recombinant DNA technology since about the early 1990's. Some of the improvements exhibited by recombinant cotton plants includes herbicide tolerance, improved fiber characteristics, and resistance to insect infestation.

The first recombinant cotton plants protected from Lepidopteran insect infestation were produced, approved by regulatory agencies for commercial distribution, and subsequently commercialized in 1996. These cotton plants contained a DNA sequence encoding a chimeric Cry1A lepidopteran insect inhibitory protein, primarily from the MON531 event. This particular trait, along with an adjacent linked DNA sequence encoding a selectable marker, has been transferred by conventional breeding into a number of cotton varieties, each of which are particularly suited for enhanced production of cotton in diversified geographic locations throughout the world. These recombinant varieties have enjoyed a tremendous commercial success for a number of reasons. One reason is that yields per acre of cotton production have on average improved dramatically because of reduced insect infestation as a result of the presence of the insect inhibitory protein present within each cell of the cotton plant. Another principle reason for the commercial success has been the reduced labor and expense due to the reduction in applications of chemical pesticides required to protect the crop from insect infestation. In addition, the reduction in chemical pesticide applications improves the overall health of the environment by avoiding the annihilation of insects or arachnids and other species which present no material threat to the crop in the field, reduces the load of chemical pesticide toxins applied to the environment, and allows the farmer to avoid the risks associated with the potentially harmful effects of exposure to chemical pesticides.

It soon became apparent that a product with a broader range of efficacy against insects would be desirable. While it may be seen as simple in view of the chemical arts to provide a combination of insect inhibitory proteins for this purpose and possibly to delay or prevent toxin resistance from being developed in the target insect population, in reality the development of a plant meeting these characteristics is problematic, and requires a great deal of resources, technical ability, and trial and error experimentation in order to obtain a single recombinant plant transformation event which results in a morphologically normal plant exhibiting the desired combination of insect inhibitory proteins produced in sufficient levels and at appropriate times during the plant growing season and in the tissues upon which target pest species feed.

Thus, there existed a need for the development and characterization of cotton plants exhibiting the characteristics of enhanced insect resistance as a result of the presence of two or more insect inhibitory proteins produced from DNA sequences incorporated into the genome of the plant cells. Furthermore, it would be desirable for the insect inhibitory traits (i) to segregate independently of one another, (ii) to not cause any adverse effects upon the physiology and metabolism of the plant, and (ii) to have little if any adverse effect upon the yield or quality of the fiber produced from said plant.

It is advantageous to be able to detect the presence of a particular event in order to determine whether progeny of a sexual cross contain a transgene of interest. In addition, a method for detecting a particular event may be helpful for complying with regulations requiring the pre-market approval of the sale of seeds to produce transgenic crop plants and foods derived from such plants, for example, or for use in environmental monitoring, monitoring traits in crops in the field, or monitoring products derived from a crop harvest, as well as for use in ensuring compliance of parties subject to regulatory or contractual terms.

It is possible to detect the presence of a transgene by any nucleic acid detection method known in the art including but not limited to thermal amplification (PCR™) or DNA hybridization using nucleic acid probes. Typically, for the sake of simplicity and uniformity of reagents and methodologies for use in detecting a particular DNA construct that has been used for transforming various plant varieties, these detection methods generally focus on frequently used genetic elements, such as promoters, terminators, marker genes, etc., because for many DNA constructs, the coding sequence region is interchangeable. As a result, such methods may not be useful for discriminating between separate events produced from the same DNA construct or very similar constructs. These methods can be used, however, if the sequence of chromosomal DNA adjacent to the inserted DNA ("flanking DNA") is known. An event-specific thermal amplification (PCR™) assay is discussed, for example, by Windels et al. (*Med Fac. Landbouww, Univ. Gent* 64/5b: 459–462, 1999), who identified glyphosate tolerant soybean event 40-3-2 using a thermal amplification primer set spanning the junction between the insert and flanking DNA. Specifically, one primer included sequence from within the insert and a second primer included sequence from flanking DNA. Such a method was also developed for event MON531 and is the subject of a separate patent application.

It would be desirable to have such a method that would detect the presence of the new event of the present invention, even in the presence of event MON531. These and other advantageous advances have been achieved by the present invention.

SUMMARY OF THE INVENTION

The cotton event MON531, described above, was transformed a second time with a genetic construct named PV-GHBK11 comprising the coding sequence for Cry2Ab, an insect-inhibitory protein, and one event of this transformation effort has been selected for potential commercial introduction. It is denominated as MON15985. Because it is a new insertion event, it will segregate from the inserted cry1Ac gene of MON531 in breeding. A line of cotton containing only the MON15985 insertion is denominated as MON15985X. According to one aspect of the invention, compositions of matter for these cotton lines are provided. The cotton seeds comprising cotton event MON15985 were deposited on Sep. 29, 2000, with the American Type Culture Collection and are designated as ATCC accession number PTA-2516.

In another aspect of the invention, methods for detecting the presence of the MON15985 event are provided. DNA sequences are provided that identify the inserted DNA sequences and the native cotton flanking sequences of MON15985. From these DNA sequences primers can be designed for use in a PCR diagnostic assay. Exemplary primers are provided as are the amplicons produced by the use of such primers when amplified in the presence of MON15985 DNA.

It should be noted that the detection of a sequence diagnostic for the insertion of cotton event MON15985 may be insufficient to answer all questions about a particular seed sample. The seed line denominated MON15985 contains both that insertion and the previous one identified as MON531. Thus, in another aspect of the invention, a method for distinguishing between MON15985 and MON15985X, a line lacking the MON531 event, is provided. The method uses one or more of the previously known sequences diagnostic for MON531.

A junction sequence herein spans the point at which DNA inserted into the genome is linked to DNA from the cotton native genome flanking the insertion point, the identification or detection of one or the other junction sequences in a plant's genetic material being sufficient to be diagnostic for is the event. Included are the DNA sequences that span the insertions in cotton event MON15985 and similar lengths of flanking DNA. Examples of such diagnostic sequences are the 20-mer junction sequences of SEQ ID NO:14, SEQ ID NO:15, SEQ ID NO:16, SEQ ID NO:17 and SEQ ID NO:18; however, other sequences of as little as 15 base pairs which overlap the junctions of the insertions or the junctions of the insertions and the genomic sequence are also diagnostic and could be used. Nucleic acid amplification of genomic DNA from the event, using the primers provided herein or designed by one of ordinary skill in the art, produces an amplicon comprising such diagnostic DNA sequences. In addition, detection of the binding of oligonucleotides which bind specifically to the diagnostic sequences described herein is also diagnostic for the event.

According to another aspect of the invention, oligonucleotide sequence primer pairs for distinguishing cotton event MON15985 from the native, nontransformed, and undisturbed sequence are provided. In particular, such flanking sequence primers pairs comprise two isolated nucleic acid molecules selected from SEQ ID NO:11 or alternatively SEQ ID NO:12, the amplicon of which will overlap one or more junction sequences in the inserted DNA, depicted as reference numbers 2, 4, 6, 9, and 11 in FIG. 1. For example, one may select an isolated nucleic acid comprising at least 15 contiguous nucleotides from about base pair positions 1–361 as set forth in SEQ ID NO:11 which are from the cotton genomic DNA sequence flanking the 5' end of the inserted DNA, depicted as reference 1 in FIG. 1, and at least one isolated nucleic acid comprising at least 15 contiguous nucleotides from about base pair positions 674–1361 as set forth in SEQ ID NO:11 which are within inserted DNA, which is depicted as reference number 3 and part of 5 in FIG. 1. Additional primer pairs useful in analyzing for cotton event MON15985 comprising at least one isolated nucleic acid of at least 15 contiguous nucleotides from nucleotides 1–1885 of SEQ ID NO:11 paired with at least one isolated nucleic acid of at least 15 contiguous nucleotides from nucleotides 362–2267 of SEQ ID NO:11 can be readily devised by one of ordinary skill in the art. Similarly, primer pairs can be derived from nucleotides 1–673 of SEQ ID NO:12 and nucleotides from nucleotides 350–1361 of SEQ ID NO:12, each primer being at least fifteen nucleotides long.

According to another aspect of the invention, specific primer sets that are useful for nucleic acid amplification, for example, are provided. Specifically, SEQ ID NO:26 and SEQ ID NO:27 are a such a primer set and can be used to produce an amplicon which is diagnostic for the presence of cotton event MON15985 DNA. SEQ ID NO:28 and SEQ ID NO:29 are another such primer set. In contrast, SEQ ID NO:26 and SEQ ID NO:29 are capable of producing an amplicon from DNA samples obtained from other than cotton event MON15985, and from hemizygous genomes comprising the wild type sequence at the point at which the MON15985 sequence integrated into the genome as well as the MON15985 integrant sequence, and said amplicon would appear to be diagnostic for the absence of inserted DNA from cotton event MON15985 in a sample, and produce no amplicon in a sample containing DNA of that event. Caution should be exercised in interpreting such a result, however, and one skilled in the art would recognize that when present as a hemizygous member of a chromosome pair, the use of SEQ ID NO:26 and SEQ ID NO:29 as a diagnostic tool for proving a negative or a positive may be erroneous.

According to another aspect of the invention, methods of detecting the presence of DNA corresponding to the cotton event MON15985 in a sample are provided. Such methods comprise: (a) contacting the sample comprising DNA with a primer set that, when used in a nucleic-acid amplification reaction with genomic DNA from cotton event MON15985, produces an amplicon that is diagnostic for cotton event MON15985; (b) performing a nucleic acid amplification reaction, thereby producing the amplicon; and (c) detecting the amplicon.

According to another aspect of the invention, methods of detecting the presence of DNA corresponding to the cotton event MON15985 in a sample, such methods comprising: (a) contacting the sample comprising DNA with a probe that hybridizes under stringent hybridization conditions with genomic DNA from cotton event MON15985 and does not hybridize under the stringent hybridization conditions with DNA from a control cotton plant; (b) subjecting the sample and probe to stringent hybridization conditions; and (c) detecting hybridization of the probe to the DNA.

Another aspect of the present invention are methods and compositions for detecting the presence of a target site, i.e., at least one of the junctions, identification or detection of which would be diagnostic for the presence of the integrated DNA with the genomic of the cotton plant in the cotton event MON15985, in a sample of nucleic acid derived from or obtained from the genome of the cotton event MON15985, using a variety of detection methods including TAQMAN (Perkin Elmer) or related flourophore/quencher methodologies, thermal amplification, ligase chain reaction, southern hybridization, ELISA methods, and colorimetric and fluorescent detection methods. In particular, the present invention provides for kits for detecting the presence of the target sequence, i.e., at least one of the junction sequences in the cotton event MON15985, in a sample containing genomic nucleic acid from the cotton event MON15985. The kit is comprised of at least one polynucleotide capable of binding to the target site or substantially adjacent to the target site and at least one means for detecting the binding of the polynucleotide to the target site. The detecting means can be selected from the group consisting of fluorescent, chemiluminescent, calorimetric, or isotopic and can be coupled at least with immunological methods for detecting the binding. A kit is also envisioned which can detect the presence of a target site in a sample, i.e., at least one of the junctions of the insert DNA with the genomic DNA of the cotton plant in the MON15985 event, taking advantage of two or more polynucleotide sequences which together are capable of binding to nucleotide sequences adjacent to or within about 100 base pairs, or within about 200 base pairs, or within about 500 base pairs or within about 1000 base pairs of the target sequence and which can be extended toward each other to form an amplicon which contains at least the target site.

The foregoing and other aspects of the invention will become more apparent from the following detailed description and accompanying drawing.

DRAWING

FIG. 1 is a graphical representation of the sequence alignment for the DNA which is flanking the inserted sequences and the inserted sequences themselves, including the cry2Ab gene in cotton event MON15985. The inserted DNA is depicted as a single strand with 5' from the left through 3' to the right. Individual DNA sequences identified herein are labeled as follows: reference number 1 is the 5' end flanking genome sequence (SEQ ID NO:19); reference number 2 is the junction sequence overlapping the sequences overlapping reference numbers 1 and 3, a diagnostic sequence as set forth in SEQ ID NO:14; reference number 3 is a chloroplast related sequence of extraneous DNA (SEQ ID NO:20); reference number 4 is the junction sequence overlapping the sequences of reference numbers 3 and 5, a diagnostic sequence as set forth in SEQ ID NO:15; reference number 5 is a remnant of cotton genome sequence (SEQ ID NO:21); reference number 6 is the junction sequence overlapping the sequences of reference numbers 5 and 7, a diagnostic sequence as set forth in SEQ ID NO:16; reference number 7 is a portion of the 5' end of the intentionally inserted sequence (SEQ ID NO:22); reference number 8 is a portion of the 3' end of the intentionally inserted sequence (SEQ ID NO:23); reference number 9 is the junction sequence overlapping the sequences of reference numbers 8 and 10, a diagnostic sequence as set forth in SEQ ID NO:17; reference number 10 is another unintentionally inserted remnant of cotton genome sequence (SEQ ID NO:24); reference number 11 is the junction sequence overlapping the sequences of reference numbers 10 and 12, a diagnostic sequence as set forth in SEQ ID NO:18; and reference number 12 is the 3' flanking cotton genome sequence, as set forth in SEQ ID NO:25.

DETAILED DESCRIPTION OF THE PREFERRED EMBODIMENTS

Cotton, *Gossypium hirsutum*, has been genetically modified to resist Lepidopteran pests, which have a negative impact on cotton production. This was accomplished by the insertion of a first DNA cassette that encodes the insecticidal Cry1Ac protein from *Bacillus thuringiensis* and a second DNA cassette that encodes the insecticidal Cry2Ab protein from *Bacillus thuringiensis*. This invention relates preferably to plants, plant parts, progeny plants which contain at least the sequences comprising the second DNA cassette, and to methods and compositions of matter for use in detecting the presence of said sequences in a sample.

The first DNA cassette was inserted into the genome of cotton cultivar Coker 312 through *Agrobacterium* sp transformation using a DNA fragment derived from plasmid PV-GHBK04 (pMON10518 in U.S. Pat. No. 5,500,365) to produce cotton event MON531, which has been bred with many different cotton varieties and successfully introduced in cotton markets around the world. Cotton event MON531 was retransformed using particle acceleration technology with a gel purified linear DNA fragment, i.e., the second cassette indicated herein and above, from plasmid PV-GHBK11 (alternatively termed pB1579), which contained cry2Ab and β-glucuronidase (uidA) coding regions. (John, M. E. 1997. *Cotton Crop Improvement Through Genetic Engineering*. Critical Reviews in Biotechnology, 17 (3): 185–208). The uidA gene was used as a selectable marker to aid in identifying cells which contained the cry2Ab coding region. The cry2Ab coding region derived from plasmid PV-GHBK11 comprises the cauliflower mosaic virus (CaMV) 35S promoter with a duplicated enhancer region (U.S. Pat. Nos. 5,530,196; 5,424,200; and 5,359,142) operably connected to a petunia heat shock protein untranslated leader sequence (PetHSP70-leader) operably connected or linked to the N-terminal chloroplast transit peptide from *Arabidopsis thaliana* EPSPS gene (AEPSPS/CTP2) (Van den Broeck, et. al. 1985. *Targeting of a foreign protein to chloroplasts by fusion to the transit peptide from the small subunit of ribulose 1,5-bisphosphate carboxylase*. Nature 313, 358–63.) operably connected or linked to a synthetic sequence encoding Cry2Ab protein (Widner, W. R. and Whiteley, H. R. 1990. *Location of the Dipteran Specificity Region in a Lepidopteran-Dipteran Crystal Protein from Bacillus thuringiensis*. J. Bacteriol. 172,2826–32.) which is operably connected or linked to the 3' nontranslated region of the nopaline synthase (NOS) gene from *Agrobacterium tumifaciens* which terminates transcription and directs polyadenylation (Fraley, R. T., et al. 1983. *Expression of bacterial genes in plant cells*. Proc Natl Acad Sci U.S.A., 80 (15), 4803–07.). The β-glucuronidase coding region is also controlled by an enhanced CaMV 35S promoter and a NOS 3' polyadenylation sequence. The insertion of the cassette, or substantially all of the cassette, containing the cry2Ab and uidA coding sequences into the cotton event MON531 gave rise to an event designated as MON15985 which comprises both the cry1A coding sequence as well as the cassette encoding the cry2Ab coding sequence. Genetic analysis of the MON15985 event has demonstrated that the two inserted cassettes are on different chromosomes and thus can be segregated in breeding, the segregants giving rise to the original MON531 event genotype as well as a second genotype designated as MON15985X comprising only a single inserted cassette comprising the gene responsible for encoding the Cry2Ab protein. It is the transformation event giving rise to the cotton genotype MON15985 as well as the MON15985X genotype which are intended as the subject matter of this invention.

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular,* 5th edition, Springer-Verlag: New York, 1991; and Lewin, *Genes V,* Oxford University Press: New York, 1994. The nomenclature for DNA bases as set forth at 37 CFR § 1.822 is used.

Comprising

As used herein, the term "comprising" means "including but not limited to."

Event

As used herein a transgenic "event" refers to a recombinant plant produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that include the heterologous DNA. Even after repeated backcrossing to a recurrent parent, the inserted DNA and flanking DNA from the transformed parent is present in the progeny of the cross at the same chromosomal location. The term "event" also refers to DNA from the original transformant comprising the inserted DNA and flanking sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

Probes and Primers

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from cotton event MON15985 (whether from a cotton plant or from a sample that includes DNA from the event). Probes according to the present invention include not only deoxyribonucleic or ribonucleic acids but also polyamides and other probe materials that bind specifically to a target DNA sequence and can be used to detect the presence of that target DNA sequence.

"Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs or sets can be used for amplification of a nucleic acid sequence, e.g., by the polymerase chain reaction (PCR™), also known as thermal amplification methods, or other conventional nucleic-acid amplification methods.

Probes and primers may be as small as ten nucleotides, but are generally 15 nucleotides or more in length, preferably 20 nucleotides or more, more preferably 25 nucleotides, and most preferably 30 nucleotides or more. Such probes and primers hybridize specifically to a target sequence under high stringency hybridization conditions. Preferably, probes and primers according to the present invention have complete sequence complementarity with the target sequence, although probes differing from the target sequence and which retain the ability to hybridize to target sequences may be designed by conventional methods. Any reference to a specific sequence for a probe or primer or other DNA sequence includes its complementary sequence.

Methods for preparing and using probes and primers are described, for example, in *Molecular Cloning: A Laboratory Manual,* 2nd ed., vol. 1–3, ed. Sambrook et al., Cold Spring Harbor Laboratory Press, Cold Spring Harbor, N.Y., 1989 (hereinafter, "Sambrook et al., 1989"); *Current Protocols in Molecular Biology,* ed. Ausubel et al., Greene Publishing and Wiley-Interscience, New York, 1992 (with periodic updates) (hereinafter, Ausubel et al., 1992); and Innis et al., *PCR Protocols: A Guide to Methods and Applications,* Academic Press: San Diego, 1990. PCR™-primer pairs can be derived from a known sequence, for example, by using computer programs intended for that purpose such as Primer (Version 0.5, © 1991, Whitehead Institute for Biomedical Research, Cambridge, Mass.).

Primers and probes based on the flanking DNA and insert sequences disclosed herein can be used to confirm (and, if necessary, to correct) the disclosed sequences by conventional methods, e.g., by re-cloning and sequencing such sequences.

Nucleic-Acid Hybridization; Stringent Conditions; Specific

The nucleic-acid probes and primers of the present invention hybridize under stringent conditions to a target DNA sequence. Any conventional nucleic acid hybridization or amplification method can be used to identify the presence of DNA from a transgenic event in a sample.

The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52–9.55. See also, Sambrook et al., 1989 at 9.47–9.52, 9.56–9.58; Kanehisa, *Nucl. Acids Res.* 12:203–213, 1984; and Wetmur and Davidson, *J. Mol. Biol.* 31:349–370, 1968.

Regarding the amplification of a target nucleic-acid sequence (e.g., by PCR™) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product.

The term "specific for (a target sequence)" indicates that a probe or primer hybridizes under stringent hybridization conditions only to the target sequence in a sample comprising the target sequence.

Nucleic-Acid Amplification

As used herein, "amplified DNA" or "amplicon" refers to the product of nucleic-acid amplification of a target nucleic-acid sequence that is part of a nucleic acid template. For example, to determine whether the cotton plant resulting from a sexual cross contains an transgenic event genomic DNA from a cotton plant may be subjected to nucleic acid amplification using a primer pair that includes a primer derived from flanking sequence in the genome of the plant adjacent to the insertion site of inserted heterologous DNA and a second primer derived from the inserted heterologous DNA to produce an amplicon that is diagnostic for the presence of the event (e.g., the amplicon is of a length and has a sequence that is diagnostic for the event). Alternatively, a primer pair can be derived from flanking sequence on both sides of the inserted DNA so as to produce an amplicon that includes the entire insert.

Nucleic-acid amplification can be accomplished by any of the various nucleic-acid amplification methods known in the art, including the polymerase chain reaction (PCR™). A variety of amplification methods are known in the art and are described, inter-alia, in U.S. Pat. Nos. 4,683,195 and 4,683,202 and in *PCR Protocols: A Guide to Methods and Applications*, ed. Innis et al., Academic Press, San Diego, 1990. Any well known method for nucleic acid amplification may be used in the practice of the present invention.

The sequence of the heterologous DNA insert or flanking sequence from cotton event MON15985 can be verified (and corrected if necessary) by amplifying such sequences from the event using primers derived from the sequences provided herein followed by standard DNA sequencing.

Detection Kit

As used herein, "detection kit" refers to a kit used to detect the presence or absence of DNA from a MON15985 event in a sample comprising nucleic-acid probes and primers of the present invention, which hybridize under stringent conditions to a target DNA sequence, and other materials necessary to enable nucleic acid hybridization or amplification methods. Alternatively, a detection kit may comprise materials necessary to enable one skilled in the art to perform methods similar to those described in PCT International Application WO 97/22719, incorporated herein by reference, to detect the presence or absence of DNA from a MON15985 event in a sample.

EXAMPLE 1

Cotton, *Gossypium hirsutum*, has been genetically modified to resist Lepidopteran pests, which have a negative impact on cotton production. This was accomplished as indicated herein by the insertion of a DNA cassette which encodes the insecticidal Cry1Ac protein from *Bacillus thuringiensis* into the genome of cotton cultivar Coker 312 through *Agrobacterium* sp transformation using a DNA fragment derived from plasmid PV-GHBK04 (pMON10518 in U.S. Pat. No. 5,500,365). This transformation resulted in three separate insertions into the cotton genome. The primary, functional insert responsible for expressing the Cry1Ac protein in cotton event 531 comprises the enhanced 35S promoter described above, cry1Ac coding region, and termination sequence linked to a sequence which encodes an antibiotic selectable marker. A second insert adjacent to and immediately upstream of the first inserted sequence comprises a partial cry1Ac coding region and termination sequence. The third insert comprises only a partial termination sequence and has been shown to segregate independently from the first two sequences indicated above. The first and second inserted sequences are tightly linked and therefore do not segregate from each other. Cotton genome sequence flanks the 5' and 3' ends of all three inserts. Therefore, six unique cotton genome/insert junctions were created as a result of the transformation-process. Any of the six junctions could be analyzed for in determining if the MON531 event is present in a cotton seed sample.

Molecular analyses were performed on cotton event MON531 to define the end of one of the transgene DNA insertions and identify the cotton genomic DNA flanking the transgene DNA inserts. Genome walking studies combined with nucleotide sequencing yielded the DNA sequences of two said cotton genome/insert junctions for the primary insert, SEQ ID NO:1 and SEQ ID NO:2 and their complements. The flanking sequences and insert sequences diagnostic for MON531 were then identified as follows: SEQ ID NO:3, the sequence of the 5' end of the primary insert; SEQ ID NO:4, the cotton genome sequence flanking that 5' end; SEQ ID NO:5, the sequence of the insert at the 3' end; and SEQ ID NO:6, the genome sequence flanking that 3' end. As discussed above, primers can be derived from these sequences to use in DNA amplification methods. Examples are SEQ ID NO:7 and SEQ ID NO:8. SEQ ID NO:9 is the sequence of a section of DNA which overlaps cotton genome DNA and one end of the inserted DNA; SEQ ID NO:10 is the sequence of a section of DNA which overlaps cotton genome DNA and the opposite end of the inserted DNA.

The following provides a nonlimiting example of how one might use these novel nucleic acid sequences to detect cotton event MON531 in a sample, including the seed line denominated MON15985, and to check for its absence in the seed line denominated MON15985X.

DNA Isolation for PCR™ Analyses.

DNA from cotton event MON531 was extracted from seed tissue. DNA was extracted from both seed and leaf tissues from the control substance (non-transgenic cotton seed and leaf tissue). DNA from seed was isolated by processing the seed to a fine powder using a commercially available blender. Approximately 2 g of the processed seed was transferred to a 50 ml conical tube, and ~16 ml of CTAB extraction buffer [1.5% (w:w) CTAB, 75 mM Tris-HCl pH 8.0, 100 mM EDTA pH 8.0, 1.05 M NaCl, and 0.75% (w:w) PVP (MW 40,000)] was added to the processed seed. The samples were incubated at 65° C. for approximately 30 minutes with intermittent mixing and then allowed to cool to room temperature. An equal volume (~16 ml) of room temperature chloroform:isoamyl alcohol (24:1 (v/v)) or chloroform was added to the samples. The suspension was mixed by inversion, and the two phases separated by centrifugation at ~16,000×g for 5 minutes. The aqueous (top) layer was removed using a transfer pipet and placed into a clean 50 ml conical tube. Approximately 1/10 volume (~1.6 ml) of 10% CTAB buffer [10% (w:w) CTAB and 0.7 M NaCl] was added to the aqueous phase, which was then mixed by inversion. The samples were centrifuged at ~16,000×g for 5 minutes to separate the phases. The aqueous (upper) phase was removed, mixed with an equal volume (~15 ml) of CTAB precipitation buffer [1% (w:w) CTAB, 50 mM Tris pH 8.0, and 10 mM EDTA pH 8.0] and allowed to stand at room temperature for approximately 1 hour. The samples were centrifuged at ~10,000×g to pellet the DNA, the supernatant was decanted, and the pellet was dissolved in approximately 2 ml of high salt TE [10 mM Tris-HCl pH 8.0, 10 mM EDTA pH 8.0, and 1 M NaCl] by incubating at 37° C. with gentle swirling for approximately 2 hours. Centrifugation was performed at ~23,000×g to pellet any remaining impurities. The supernatant was removed, placed into a clean 15 ml tube, and approximately 1/10 volume (~150 µl) of 3M NaOAc, pH 5.2, and 2 volumes (4 ml relative to the supernatant) of chilled 100% ethanol were added to precipitate the DNA. The precipitated DNA was spooled into a microfuge tube containing approximately 1 ml of 70% ethanol. The DNA was pelleted in a microfuge at maximum speed (14,000 rpm) for 5 minutes, dried, and re-dissolved in TE, pH 8.0 in a 4° C. refrigerator overnight.

The non-transgenic cotton genomic DNA used as a control was isolated from leaf tissue that was frozen in liquid nitrogen and ground into a fine powder using a mortar and pestle. Approximately 1 g of the ground leaf tissue was transferred to a 13 ml centrifuge tube and 6 ml of extraction buffer [2.5 ml DNA extraction buffer (350 mM sorbitol, 100 mM Tris pH 7.5, 5 mM EDTA, 0.38% (w/v) sodium bisulfite), 2.5 ml nuclei lysis buffer (200 mM Tris pH 7.5, 50 mM EDTA, 2 M NaCl, 2% (w/v) CTAB), and 1 ml Sarkosyl (5% (w/v) solution)] was added. The samples were incubated at 65° C. for approximately 30 minutes with intermittent mixing. Four and a half milliliters of chloroform:isoamyl alcohol (24:1 (v/v)) at room temperature was added to the samples. The suspension was mixed for 2 to 3 minutes, and the two phases separated by centrifugation for 15 minutes at ~2,000×g at 4° C. The aqueous (top) layer was removed using a transfer pipette and placed into a 13 ml centrifuge tube. Five milliliters of 100% isopropanol were added, and the tubes were mixed by inversion to precipitate the DNA. The precipitated DNA was spooled into a microfuge tube containing 500 µl of 70% ethanol. The DNA was pelleted in a microfuge at maximum speed (14,000 rpm) for 2 minutes. The DNA was dried and dissolved in TE buffer in a 4° C. refrigerator overnight.

PCR™ Verification of Unique Insert-Cotton Genome Junctions in Cotton Event MON531.

The DNA sequences of four cotton genome/insert junctions were identified using the PCR™ based Universal Genome Walker Kit™ as per the manufacturer's protocol followed by nucleotide sequencing of the PCR™ products. Next, PCR™ assays were developed using one primer complementary to cotton genomic DNA and another primer complementary to inserted trans-gene DNA. For example, one primer designed to the 3' end of the primary, functional insert complementary to genomic flanking sequence (e.g., SEQ ID NO:6) paired with a second primer at the 3' end of the primary, functional insert complementary to inserted transgene sequence (e.g., SEQ ID NO:5). The PCR™ assays were performed using 10–100 ng of cotton event MON531 genomic DNA template in a 50 µl reaction volume containing a final concentration of 1.1 mM $Mg^{2+}$, 0.4 µM of each primer, 200 µM each dNTP, and 2.5 units of Taq DNA polymerase. The reactions for the PCR™ assays were performed under the following cycling conditions: 1 cycle at 94° C. for 3 minutes; 38 cycles of 94° C. for 30 seconds, 60° C. for 30 seconds, 72° C. for 90 seconds; 1 cycle at 72° C. for 10 minutes. The PCR™ products were separated using agarose gel electrophoresis, visualized by ethidium bromide staining, excised from the gel, and subjected to DNA sequencing using dye-terminator chemistry to confirm the sequences.

In the example above, as expected, the control reactions without template DNA and Coker 312 non-transgenic negative control DNA did not generate a PCR™ product. The cotton event MON531 samples generated the expected size PCR™ products of 264 bp for the 3' flanking sequence. Therefore, the novel nucleic acid sequences at the junction of inserted DNA and cotton genomic DNA in cotton event MON531 are useful for detecting DNA derived from cotton event MON531 in a sample.

MON531 in the variety Coker 312 background was crossed into the variety DP50 (Delta & Pine Land Company) to produce a variety containing the MON531 event encoding the Cry1Ac protein, which was designated as DP50B.

EXAMPLE 2

This example describes the production of a transformed cotton plant designated as MON15985 derived from DP50B which contains an additional insertion event encoding a Cry2Ab insect inhibitory protein, and the isolation and characterization of the 5' and 3' DNA sequences flanking the 5' and 3' ends of the MON15985.

Target DP50B plant cells were transformed using particle acceleration technology with a linear DNA segment derived from plasmid PV-GHBK11. The linear DNA segment was prepared by digestion of plasmid PV-GHBK11 with the restriction enzyme KpnI, separation of the plasmid fragments by agarose gel electrophoresis and isolation of the DNA segment containing cassette comprising the cry2Ab coding sequence and uidA coding sequence (GUS). No plasmid backbone was contained within the segment or sequence isolated and purified and prepared for bombardment of cotton tissue. The expression cassette consists of a cry2Ab coding region regulated by an enhanced CaMV 35S plant expressible promoter and an *Agrobacterium tumefaciens* NOS3' transcription termination and polyadenylation sequence. The cry2Ab coding sequence is designed to target the expression product as a precursor protein for chloroplast import in plant cells (as disclosed in WO 0026371 and U.S. patent application Ser. No. 09/186,002, filed Nov. 4, 1998, the entire contents of which are incorporated herein by reference).

The cotton variety DP50B was transformed with the DNA cassette described above by bombardment with DNA coated gold particles using electrostatic discharge method (John, M. E., Cotton Crop Improvement Through Genetic Engineering. Critical Reviews in Biotechnology, 17:185–208 (1997)). Different events were screened for efficacy against insect pests, phenotype, and genetic segregation for expression of the Cry2Ab protein. Based on these criteria, 6 lines were chosen for further characterization of the insertion event. Southern blot was used as the primary method for evaluating the presence of one or more copy numbers of insertion and completeness of the insertion event. One line, 15985, was chosen for a thorough molecular characterization of the insertion event that inserted into the DP50B genome. The DNA surrounding the insertion event was isolated and characterized.

Isolation of the DNA flanking the insertion event: DNA was extracted from young cotton leaves by a modified Phyto-Pure® method from Amersham which is designed to extract DNA from plants with large amounts of contaminating carbohydrates. In order to determine the sequence of the DNA around the inserted cry2Ab coding sequence, the Genome Walker® protocol from CloneTech, Inc. was used. The manufacturer's recommended conditions were followed with only one modification: rather than using phenol extraction for purification of the DNA after restriction endonuclease cleavage, the DNA was purified with a Qiagen QIAquick® spin column in accordance with the manufacturer's instruction manual.

The enzymes used to cut the genomic DNA prior to linker ligation were DraI, PvuII, ScaI and StuI. Following the procedure provided by Qiagen, the DNA was extracted in 5 volumes of PB buffer, bound to the column, washed with 0.75 ml of PE and then eluted from the column into 20 mL of 10 mM Tris pH 8.5. This DNA was then used as the source for the linker libraries. Primer positions were deliberately chosen away from the ends of where the DNA was linearized to allow for a certain amount of deletion at either end. The first primers (SEQ ID NO:30 and SEQ ID NO:31) were designed to anneal to sequences that are unique to a cry2Ab coding sequence because of the presence of repeated DNA elements in the cotton genome. The resulting PCR™ products were subjected to a second PCR™ reaction using nested primers directly adjacent to those used in the first reaction (SEQ ID NO:32 and SEQ ID NO:33). The PCR™ parameters used were those recommended by CloneTech. The primary amplification parameters were as follows: 7 cycles 94° C. 2 sec, 72° C. 3 min, 32 cycles 94° C. 2 sec, 68° C. 3 min, and secondary amplification parameters were as follows: 5 cycles 94° C. 2 sec, 72° C. 3 min, 20 cycles 94° C. 2 sec, 68° C. 3 min, and 68° C. 4 min in last cycle. All PCR™ reactions were performed on a Perkin-Elmer 9700 machine.

The resulting PCR™ products from the second amplification were cloned into the pBS(SK+) vector from Stratagene which had been cut with SmaI to generate a blunt end and treated with alkaline phosphatase to prevent self-ligation. The DNA fragments that were generated in the secondary PCR™ reaction were treated with T4 DNA kinase to add a 5' phosphate and then ligated into the blunt end vector under standard ligation conditions.

Genome Walkers® protocol: The secondary PCR™ reactions using the nested primer pairs produced multiple fragments synthesized from both 5' and 3' ends. Three independent fragments for the 5' end were cloned and sequenced using methods well-known in the art, while two fragments were cloned and sequenced from the 3' end. For each individual fragment, at least two independent clones were obtained.

The sequence of the clones from each primer set were compared to one another. The sequences among the respective clones were determined to be the same, and contained the same plant trans-gene junction.

EXAMPLE 3

This example illustrates how the DNA sequences flanking the MON15985 insertion event can be used to determine zygosity.

Design and development of a PCR™ based test for homozygosity of the MON15985 insertion event: The DNA sequence of the two regions flanking the MON15985 insertion event was used to design a PCR™ based homozygosity test. Such a test would be considered useful if it were able to detect both the specific MON15985 insertion event and the wildtype chromosome. To test the feasibility of developing an assay that also detects the wild type chromosome, primers were designed from the sequence directly adjacent to the insertion event to test if they could be used to synthesize a DNA fragment in the non-transgenic cotton, as well as in the 15895 line. The primers chosen were capable of synthesizing the whole MON15985 insertion event, but no product was observed in the non-transgenic controls. These results indicated that the insertion event was not a simple break in the DNA and insertion of the DNA sequence and cassette encoding the Cry2Ab protein. This result, however, established that the two ends are indeed connected and flank an intact gene cassette containing cry2Ab.

Primers were designed to the nucleic acid sequence flanking the 3' end of the insert to amplify fragments via the Genome Walker® protocol in linker libraries made from non-transgenic cotton DNA. A 620 base pair fragment was cloned and sequenced from non-transgenic cotton. This sequence was then used to design primers for the wild type chromosome that would be present in the heterozygous individual. Several sets of primers were made and tested together in order to find a set that worked in a single reaction and provided no background bands. A primer set comprising SEQ ID NO:34 (3' cotton plant flanking sequence) and SEQ ID NO:35 (5' cotton plant flanking sequence) was found to produce an 800 base pair amplicon from wild type, or non-transgenic cotton DNA. However, if at least one insert is present, the primer comprising SEQ ID NO:36 will anneal to cry2Ab specific sequences and generate a 1.5 kb amplicon with a primer annealing to the 3' cotton plant flanking sequence (SEQ ID NO:34). Therefore, the resulting assay using PCR™ primers comprising SEQ ID NO:36, SEQ ID NO:34, and SEQ ID NO:35 is as follows: if an individual is homozygous for the MON15985 insertion event then only one band of 1.5 kb would be present; but if it is heterozygous then an additional 0.8 kb band would also be present.

Both of these bands (1.5 kb and 0.8 kb) were cloned and sequenced to confirm their identity. The DNA sequence of the 800 base pair fragment generated in heterozygous individuals is identical to the sequence of the Genome Walker® fragment generated with the primers from the 3' end and non-transgenic DNA.

Confirmation of PCR™ based zygosity assay: To verify the precision of the zygosity assay a series of experiments were conducted utilizing known homozygous, heterozygous and negative transgenic progeny of MON15985.

R2:

Phenotype: Fifteen individual R2 plants from three suspected R1 genotypes were characterized for the presence or absence of the Cry2Ab protein via ELISA. Plants of interest that were positive for the study included MON15985-2 and MON15985-34. Plant MON15985-71 was identified as negative for Cry2Ab protein.

R3:

Phenotype: Fifteen individual R3 seeds from each of the selected R2 plants were planted in 4" pots and subsequently screened for the presence of the Cry2Ab protein via qualitative ELISA. The ELISA results reported that all R3 plants of MON 15985-2 were positive, thus giving the R2 parent a designation of being homozygous for the cry2Ab gene. R3 progeny of MON15985-34 were a mixture of positive and negative plants giving the R2 parent a designation of being heterozygous for the cry2Ab gene. All R3 plants of MON15985-71 were negative and confirmed that the R2 parent was negative as well.

Genotype: A PCR™-based zygosity assay was performed on five R3 plants of MON15985-2 and MON15985-71. Primers and techniques were used as previously described. Results of this test gave the expected banding patterns. All progeny of MON15985-2 produced only the single 1.5 kb band supporting the ELISA data, which indicated the MON15985-2 line is homozygous positive for the cry2Ab gene. All progeny of MON15985-71 produced only the single 0.8 kb band found in the wild-type, thus supporting the ELISA results in demonstrating that this line is homozygous negative for the cry2Ab gene. Five progeny of each of fourteen individual R2 families of MON15985-34 were screened as well giving combinations of homozygous, heterozygous and negative plants.

R4:

Five individual plants from all three R3 populations were allowed to self pollinate and were taken to harvest. Fifteen R4 progeny from each of the R3 plants tested via PCR™ were planted in 4" pots to confirm the results on the R3 plants. Thus, if the R3 PCR™ result was homozygous then the all the R4 progeny should be homozygous, as well if the R3 PCR™ result was heterozygous the R4 progeny should be a mixture of homozygous, heterozygous and negative plants. All R4 progeny families provided the expected result based on the R3 PCR™ assay. Therefore, the PCR™ based assay provides a durable method for genotyping plants for zygosity.

EXAMPLE 4

This example illustrates the DNA sequences flanking the 5' and 3' ends of the insert in cotton event MON15985.

DNA from MON15985 was extracted from leaf tissue that was frozen in liquid nitrogen and ground into a fine powder using a mortar and pestle. Approximately 1 g of the ground leaf tissue was transferred to a 13 ml centrifuge tube and 6 ml of extraction buffer [2.5 ml DNA extraction buffer (350 mM sorbitol, 100 mM Tris pH 7.5, 5 mM EDTA, 0.38% (w/v) sodium bisulfite), 2.5 ml nuclei lysis buffer (200 mM Tris pH 7.5, 50 mM EDTA, 2 M NaCl, 2% (w/v) CTAB), and 1 ml Sarkosyl [5% (w/v) solution)] were added. The samples were incubated at 65° C. for approximately 35 minutes. Four and a half milliliters of chloroform:isoamyl alcohol [24:1 (v/v)] at room temperature were added to the samples. The suspension was mixed for 2 to 3 minutes, and the two phases separated by centrifugation for 15 minutes at ~2,000×g at 4° C. The aqueous (top) layer was removed and placed into a 13 ml centrifuge tube. Five milliliters of 100% isopropanol were added, and the tubes were mixed by inversion to precipitate the DNA. The precipitated DNA was spooled into a microfuge tube containing 500 µl of 70% ethanol. The DNA was pelleted in a microfuge at maximum speed (14,000 rpm) for 2 minutes. The DNA was dried and dissolved in TE buffer in a 4° C. refrigerator overnight.

DNA from the DP50 control was extracted from seed tissue. DNA from seed was isolated by processing the seed to a fine powder using a commercially available blender. Approximately 2 g of the processed seed was transferred to a 50 ml conical tube, and ~16 ml of CTAB extraction buffer [1.5% (w/v) CTAB, 75 mM Tris pH 8.0, 100 mM EDTA pH 8.0, 1.05 M NaCl, and 0.75% (w/v) PVP (MW 40,000)] were added to the processed seed. The samples were incubated at 65° C. for approximately 30 minutes with intermittent mixing and then allowed to cool to room temperature. An equal volume (~15 ml) of room temperature chloroform:isoamyl alcohol [24:1 (v/v)] was added to the samples. The suspension was mixed for 5 minutes, and the two phases separated by centrifugation at ~16,000×g for 5 minutes at room temperature. The aqueous (top) layer was removed and placed into a clean 50 ml conical tube. Approximately 1/10 volume (~1.5 ml) of 10% CTAB buffer [10% (w/v) CTAB and 0.7 M NaCl] and an equal volume of chloroform:isoamyl alcohol [24:1 (v/v)] were added to the aqueous phase, which was then mixed by inversion for 5 minutes. The samples were centrifuged at ~16,000×g for 5 minutes at room temperature to separate the phases. The aqueous (upper) phase was removed, mixed with an equal volume (~15 ml) of CTAB precipitation buffer [1% (w/v) CTAB, 50 mM Tris pH 8.0, and 10 mM EDTA pH 8.0] and allowed to stand at room temperature for approximately 1 hour. The samples were centrifuged at ~10,000×g to pellet the DNA, the supernatant was decanted, and the pellet was dissolved in approximately 2 ml of high salt TE [10 mM Tris-HCl pH 8.0, 10 mM EDTA pH 8.0, and 1 MNaCl] by incubating at 37° C. with gentle swirling for approximately 2 hours or by sitting in a 4° C. refrigerator overnight. Centrifugation was performed at ~23,000×g to pellet any remaining impurities. The supernatant was removed, placed into a clean 15 ml tube, and approximately 1/10 volume (~150 µl) of 3M NaOAc, pH 5.2, and 2 volumes (~4 ml relative to the supernatant) of 100% ethanol were added to precipitate the DNA. The precipitated DNA was spooled into a 5 microfuge tube containing approximately 1 ml of 70% ethanol. The DNA was pelleted in a microfuge at maximum speed (14,000 rpm) for 5 minutes, dried, and re-dissolved in TE, pH 8.0 in a 4° C. refrigerator overnight.

DNA from each of DP50 and MON15985 was quantitated prior to the initiation of the study within the study from which they were derived. DNA quantitation was conducted using a Hoefer DyNA Quant 200 Fluorometer using Boehringer Mannheim molecular size marker IX as a DNA calibration standard.

PCR analysis of the genomic sequence flanking the 5' end of the insert encoding Cry2Ab protein in cotton event MON15985 was performed using one primer derived from the 5' genomic flanking sequence paired with a second primer located in the inserted DNA near the 5' end in the enhanced CaMV 35S promoter sequence, spanning a 1894 bp region (SEQ ID NO:26 and SEQ ID NO:27). The PCR analysis for the genomic sequence flanking the 3' end of the insert encoding Cry2Ab protein in cotton event MON15985 was conducted using one primer located in the NOS 3' polyadenylation sequence near the 3' end of the insert paired with a second primer derived from the 3' genomic flanking sequence, spanning a 763 bp region (SEQ ID NO:28 and SEQ ID NO:29).

The PCR analyses were conducted using genomic DNA from the cotton event MON15985 or non-transgenic cotton line DP50. The PCR analysis was conducted using 35–50 ng of cotton event MON15985 or non-transgenic line DP50 genomic DNA template in a 50 µl reaction volume containing a final concentration of 1.5 mM $Mg^{2+}$, 0.2 µM of each primer, 200 µM each dNTP, and 2.5 units of Platinum Taq DNA polymerase (Gibco BRL). The reactions for the 5' end of the insert were performed under the following cycling conditions: 1 cycle at 94° C. for 3 minutes; 35 cycles of 94° C. for 1 minute, 56° C. for 1 minute, 72° C. for 2 minutes; 1 cycle at 72° C. for 10 minutes. The reactions for the 3' end of the insert were performed under the following cycling conditions: 1 cycle at 94° C. for 3 minutes; 35 cycles of 94° C. for 1 minute, 53° C. for 1 minute, 72° C. for 45 seconds; 1 cycle at 72° C. for 10 minutes. The PCR products were separated on a 1.0% agarose gel. Electrophoresis was conducted for approximately 1.5–2 hours at 100 V and visualized by ethidium bromide staining.

PCR products of the expected sizes containing the sequences flanking the 5' and 3' ends of the insert encoding Cry2Ab protein in cotton event MON15985 generated with two primer pairs were isolated by gel electrophoresis of 20 µl of the PCR products on 1.0% agarose gels. PCR products representing the 5' or 3' flanking sequences were excised from a gel and purified using the QIAquick Gel Extraction Kit (Qiagen) following the procedure supplied by the manufacturer. For both analyses, the purified PCR products were then sequenced with the PCR primers using dye-terminator chemistry. Due to the length of the PCR products, sequencing was performed with both the primers used to generate the products as well as primers designed internal to the amplified sequence.

PCR analyses were performed on genomic DNA extracted from cotton event MON15985 and non-transgenic cotton line DP50 to verify the DNA sequences flanking the 5' and 3' ends of the insert in cotton event MON15985. The control reaction containing no template DNA as well as the reaction containing DP50 non-transgenic cotton DNA did not generate a PCR product, as expected. PCR analysis of the cotton event MON15985 DNA generated the expected size product of 1894 bp representing the 5' flanking sequence and a portion of the 5' end of the insert encoding Cry2Ab protein.

The control reaction containing no template DNA as well as the reaction containing DP50 non-transgenic cotton DNA did not generate a PCR product, as expected. PCR analysis of the cotton event MON15985 DNA generated the expected size product of 763 bp representing the 3' flanking sequence and a portion of the 3' end of the insert. These results demonstrate that a predicted size PCR product is generated from both ends of the insert encoding Cry2Ab in the cotton event MON15985.

The consensus sequence representing the cotton genomic DNA sequence flanking the 5' end of the insert, as well as DNA at the 5' end of the insert, is represented by SEQ ID NO:11. The 5' consensus sequence data contains 1877 bp of DNA flanking the insert followed by 390 bp of insert sequence containing the enhanced CaMV 35S promoter. Base pairs 362–750 show homology to chloroplast DNA. The consensus sequence representing the cotton genomic sequence flanking the 3' end of the insert, as well as the DNA at the 3' end of the insert, is represented in SEQ ID NO:12. The 3' consensus sequence data contains 349 bp of insert sequence containing the 3' end of the NOS 3' polyadenylation sequence and polylinker sequence followed by 1012 bp of cotton genomic DNA flanking the insert. The reported 5' and 3' consensus sequences presented here are the combination of multiple sequencing reactions and are shorter than those of the PCR products used to generate the sequences. These data delineate the 5' and 3' ends of the insert in the cotton event MON15985 and show the DNA which immediately flanks the insert on both ends.

This data demonstrates that cotton event MON 15985 contains a single DNA insert containing 5 (1) a sequence encoding UidA (GUS) regulated by the enhanced 35S CaMV promoter (lacking approximately 260 bp at the 5' end) and NOS 3' polyadenylation sequence; and (2) a coding sequence encoding Cry2Ab regulated by the enhanced 35S CaMV promoter and the NOS 3' polyadenylation sequence (FIG. 1). PCR and sequence analyses performed in this example confirm the sequence of the 5' and 3' ends of the insert encoding Cry2Ab in the cotton event MON15985, and verify the genomic DNA sequence flanking the 5' and 3' ends of the insert.

EXAMPLE 5

This example illustrates the physical characteristics of the sequences flanking the cotton event MON15985, and characterizes the nature and physical location of additional DNA sequences flanking the 5' and 3' end of the inserted DNA in the cotton event MON15985. Genomic DNA was is analyzed by Southern blotting to determine the number of insertion events, the copy number of the inserted DNA, the integrity of the inserted promoters, coding regions, and polyadenylation sequences, and the presence or absence of plasmid backbone sequence. All analyses were performed with both the cotton line DP50B (control) and with the newly produced MON15985 event to characterize the newly inserted DNA. In addition, the flanking sequence of the 5' and 3' "insert-to-plant" junctions (previously determined by Genome Walking) were confirmed by PCR.

Plasmid PV-GHBK11, the source plasmid, served as the primary reference substance in these analyses. The plasmid, mixed with DNA from the DP50 control substance, was used as a size indicator and a positive hybridization control in Southern blot analysis. Additionally, molecular size markers from Boehringer Mannheim [Molecular Weight Markers II (23.1 Kb–0.6 Kb) and IX (1.4 Kb–0.072 Kb), catalog #236 250 and #1449 460, respectively] and Gibco BRL [High Molecular Weight DNA Marker (48.5 Kb–8.3 Kb) and 100 bp ladder (2.1 Kb–0.1 Kb), catalog #15618-010 and #15628-019, respectively] were used for size estimations.

Genomic DNA from insect protected cotton event MON15985 was digested with a variety of restriction enzymes and subjected to Southern blot hybridization analysis to characterize the DNA encoding Cry2Ab and GUS integrated into the genome of DP50B.

DNA extracted from leaf tissue was used for all of the analyses in this example except for the nontransgenic sample on the uidA gene cassette intactness blot probed with the NOS 3' polyadenylation sequence probe which was isolated according to the method of Rogers and Bendich (1985). Leaf tissue was frozen in liquid nitrogen and ground into a fine powder using a mortar and pestle. Approximately 1 g of the ground leaf tissue was transferred to 13 ml centrifuge tube containing 6 ml of the extraction buffer [2.5 ml DNA extraction buffer (350 mM Sorbitol, 100 mM Tris pH 7.5, 5 mM EDTA), 2.5 ml Nuclei lysis buffer (200 mM Tris pH 7.5, 50 mM EDTA, 2 M NaCl, 2% CTAB), and 1 ml Sarkosyl (5% solution)]. The samples were incubated at 65° C. for approximately 30 minutes with intermittent mixing. Four and a half milliliters of a mixture of chloroform:isoamyl alcohol (24:1) at room temperature was added to the samples. The suspension was mixed for 2 to 3 minutes, and the two phases separated by centrifugation for 15 minutes at ~1,000×g at 4° C. The aqueous (top) layer was removed using a transfer pipette and placed into a 13 ml centrifuge tube. Five milliters of 100% isopropanol were added, and the tubes were mixed by inversion to precipitate the DNA. The precipitated DNA was pelleted by centrifuging at ~1,000×g for 5 minutes at 4° C. The pellet was washed with approximately 1 ml of 70% ethanol and centrifuged for an additional 5 minutes at ~1,000×g at 4° C. The DNA was allowed to dry at room temperature and re-dissolved in TE at 4° C. overnight.

The purified genomic DNA was quantitated using a Hoefer DyNA Quant™ 200 Fluorometer (San Francisco, Calif.) with Boehringer Mannheim Molecular Weight Marker IX used as a calibration standard.

Approximately 10 µg of genomic DNA from the test and control lines were used for the restriction enzyme digests. Overnight digests were performed at 37° C. according to manufacturers protocols in a total volume of 500 µl using 100 units of restriction enzyme. Some of the control digests were spiked with either 5 or 10 pg of PV-GHBK11. All restriction enzymes were purchased from Boehringer Mannheim. After digestion, the samples were precipitated by adding 1/10 volume (~50 µl) of 3M NaOAc and 2 volumes (~1 ml relative to the original digest volume) of 100% ethanol, followed by incubation at −20° C. for at least one hour. The digested DNA was pelleted by centrifugation, washed with 70% ethanol, vacuum dried for 10–20 minutes, and re-dissolved at room temperature in either water or TE.

Digested DNA's were separated on 0.8% agarose gels in 1X TBE buffer. A 'long run' and a 'short run' were performed for each Southern blot analysis. The long run facilitated greater resolution of the higher molecular weight DNA's while the short run ensured that all smaller molecular weight DNA's were retained on the gel. The long run/short run involved a 4–6 hour electrophoresis at 80–85 V and an overnight (9–15 hour) run at 35–38 V. After electrophoresis, the gels were stained in 0.5 µg/ml ethidium bromide for 20–30 minutes and photographed.

Plasmid PV-GHBK11 DNA was isolated from overnight E. coli cultures. Probe templates homologous to the cry2Ab coding region, uidA coding region, the enhanced CaMV. 35S promoter, the NOS 3' polyadenylation sequence, and the entire backbone region were prepared by PCR using PV-GHBK11 as the template.

Approximately 25 ng of each probe template, except the NOS 3' polyadenylation sequence, were labeled with $^{32}$P-dCTP using the random priming method (RadPrime DNA Labeling System, Life Technologies). The NOS 3' polyadenylation sequence was labeled using PCR with NOS 3' template (15 ng), NOS 3' specific primers (0.25 µM each), 1.5 mM MgCl$_2$, 3 µM dATP, dGTP, and dTTP, 100 µCi of $^{32}$P-dCTP and 2.5 Units of Taq DNA polymerase in a final volume of 20 µl. The cycling conditions were as follows: 1 cycle at 94° C. for 3 minutes; 5 cycles at 94° C. for 45 seconds, 55° C. for 30 seconds, and 72° C. for 1 minute; 1 cycle at 72° C. for 10 minutes. The radiolabeled probe was purified using a Sephadex G-50 column (Boehringer Mannheim).

Southern blot analyses (Southern, 1975) were performed established procedures, generally Maniatis Fritsch Sambrook (Cold Spring Harbor). Following electrophoresis, the gel was incubated in depurination solution (0.125 N HCl) for ~10 minutes followed by denaturing solution (0.5 M NaOH, 1.5 M NaCl) for ~30 minutes, and then neutralizing solution (0.5 M Tris-HCl pH 7, 1.5 M NaCl) for ~30 minutes. The DNA from the agarose gels was transferred to Hybond-N™ nylon membranes (Amersham) using a Turboblotter™ (Schleicher & Schuell). The DNA was allowed to transfer for 4 hours to overnight (in 20×SSC) and covalently cross-linked to the membrane with a UV Stratalinker™ 1800 (Stratagene) set to autocrosslink. The blots were prehybridized an average of 2 hours in an aqueous solution of 0.5 M sodium phosphate, 7% SDS (w/v), and 0.1 mg/ml E. coli tRNA. Hybridization with the radiolabeled probe was performed in fresh prehybridization solution for 14–21 hours at approximately 65° C. Membranes were washed at least four times in an aqueous solution of 0.1% (w/v) SDS and 0.1×SSC for 15 minute intervals at 65° C. Multiple exposures of the blots were generated using Kodak Biomax MS™ film in conjunction with one Kodak Biomax MS™ intensifying screen. Blots were stripped by incubating the blot with boiling 0.1% (w/v) SDS and allowing it to cool to room temperature.

The insert number (the number of integration sites of newly introduced transgenic DNA in the cotton genome) was evaluated. The test and control DNA's were digested with the restriction enzyme ScaI, which does not cleave within the DNA segment used for transformation. This enzyme released a segment containing the inserted DNA and adjacent plant genomic DNA. The plasmid-spiked DP50 'short run' samples were also digested with XbaI to linearize the plasmid. The blot was probed with the reference plasmid PV-GHBK11.

The number of copies of the transformation cassette inserted into each locus was determined by digesting the test genomic DNA with the restriction enzyme SphI, an enzyme that cuts only once in the linear DNA segment used to generate the event. The blot was probed with the reference plasmid PV-GHBK11.

The integrity of the cry2Ab coding region was determined by digestion with a restriction enzyme, NcoI, that cleaves at the 5' and 3' ends of the cry2Ab coding region. The blot was probed with the full length cry2Ab coding region.

The integrity of the cry2Ab encoding cassette (enhanced CaMV 35S promoter, cry2Ab coding region, and NOS 3' polyadenylation sequence) was assessed by digestion with the restriction enzyme BamHI which cleaves at the 5' and 3' ends of the cry2Ab cassette. The blot was sequentially probed with each element of the cassette.

The integrity of the uidA coding region was determined by digestion with the restriction enzymes EcoRI and BglII which cleave at the 5' and 3' ends of the uidA coding region, respectively. The blot was probed with the full length uidA coding region.

The integrity of the uidA cassette (enhanced CaMV 35S promoter, uidA coding region, and NOS 3' polyadenylation sequence) was assessed by digestion with the restriction enzymes BamHI and SphI which cleave at the 5' and 3' ends of the UidA cassette. The blot was sequentially probed with each element of the cassette.

The backbone region of the plasmid is defined as the KpnI restriction fragment of PV-GHBK11 that was not used to transform the plant. It consists of a bacterial origin of replication, ori-pUC, and the nptII gene under the control of a bacterial promoter. To confirm the absence of backbone, genomic DNA was digested with the restriction enzyme KpnI and probed with the full-length backbone region.

The sequence of the 5' and 3' insert-to-plant genomic DNA junctions were determined as described above using Clontech's Universal Genome Walker™ Kit. Primers were designed to verify these junctions by PCR. The 5' junction was verified using one primer designed to the 5' genomic flanking sequence paired with a second primer in the enhanced CaMV 35S promoter of the uidA gene. The 3' junction was verified using a primer designed to the 3' genomic flanking sequence with a second primer located in the cry2Ab gene. The PCRs were conducted using 100 ng of leaf genomic DNA (1–2 µl) as a template, 10 pmol of each primer (1 µl each), and PCR Supermix (Gibco BRL cat no. 10572-014) in a 25 µl reaction volume. The amplification of the reactions was performed under the following cycling conditions: 1 cycle 94° C. for 3 minutes; 30 cycles 94° C. for 30 seconds, 55° C. for 1 minute, 72° C. for 2 minutes; 1 cycle 72° C. for 4 minutes. The PCR products were separated on a 1% agarose gel in 1X TAE and visualized by staining with ethidium bromide.

Test and control DNA samples were digested with ScaI. DP50 control DNA spiked with PV-GHBK11 was also digested with ScaI. Since ScaI does not cleave within the plasmid, a second enzyme, XbaI, was added to linearize the plasmid. The plasmid was linearized to facilitate its migration through the gel to serve as an accurate size estimator. The blot was probed with radiolabeled PV-GHBK11 (FIG. 1), the source plasmid for the linear DNA segment used in the transformation. The DP50 long run did not produce any detectable background bands. Plasmid PV-GHBK11 mixed with DP50 short run produced the expected size band at approximately 8.7 Kb, the size of the whole plasmid, with no additional bands. The DP50B long and short runs produced two bands at approximately 22 Kb and 15 Kb (very faint). Since these bands are present in both event MON15985 and the DP50B (MON531) control they are considered background bands associated with the MON531 event. The MON15985 long and short each produced one band not present in either the DP50 or the DP50B lanes at approximately 9.3 Kb. This result suggests that cotton event MON15985 contains one segment of integrated DNA located on a 9.3 Kb ScaI restriction fragment.

Genomic DNA isolated from MON15985, DP50B, DP50 (non-transgenic control) and DP50 mixed with plasmid PV-GHBK11 DNA was digested with SphI. The blot was probed with PV-GHBK11, the source plasmid for the linear DNA segment used in transformation. The DP50 long run did not produce any detectable background bands. Plasmid PV-GHBK11 mixed with DP50 in the short run produced the expected size bands at 3.9 and 4.8 Kb; an additional faint band at 8.7 Kb in lane 5 is presumably due to undigested plasmid DNA. The DP50B long and short runs produced three bands at approximately 6.4, 8.3, and 8.6 Kb. Since these bands are present in both event MON15985 and the DP50B control they are considered background bands associated with the MON531 event. The MON15985 long and short runs each produced two bands not present in the DP50 or the DP50B lanes at approximately 2.3 Kb and 3.5 Kb. Because the enzyme SphI cuts only once within the transformation cassette, this result suggests that MON15985 contains one copy of integrated DNA which produces these two restriction fragments.

DNA from the test, controls, and control mixed with plasmid PV-GHBK11 DNA was digested with NcoI to release the cry2Ab coding region and assess its intactness. The blot was probed with the full-length cry2Ab coding region. As expected, the DP50 non-transgenic control long run and the DP50B control long and short runs showed no detectable hybridization bands. Plasmid PV-GHBK11 mixed with DP50 in the short run produced the expected ~1.9 Kb band which corresponds to the entire cry2Ab coding region. Both the MON15985 long and short runs also produced a 1.9 Kb band which corresponds to the expected size of an intact cry2Ab coding region. This result establishes that event MON15985 contains the intact cry2Ab coding region, with no additional detectable fragments.

DNA from the test, controls, and control mixed with plasmid PV-GHBK11 DNA was digested with BamHI which releases the entire cassette encoding Cry2Ab (i.e. cry2Ab coding region, the enhanced CaMV 35S promoter, and the NOS 3' polyadenylation sequence).

The blot was probed with the full length cry2Ab coding region. The DP50 non-transgenic control long run and the DP50B control long and short runs showed no detectable hybridization bands. Plasmid PV-GHBK11 mixed with DP50 in the short run produced the expected 3.2 Kb band which corresponds to the entire cassette encoding Cry2Ab. Both the MON15985 long and short runs produced a band at approximately 4.0 Kb. This result indicates that the 3' end of the transformation cassette lost the BamHI restriction site during integration into the cotton genome. The 3' sequence of the insert-to-plant junction, previously determined by genome walking, was verified by PCR analysis. Sixty-six base pairs of the 3' end of the transformation cassette were shown to have been deleted, including the BamHI site. The deleted nucleotides do not include any of the NOS 3' polyadenylation sequence associated with the cassette encoding Cry2Ab, but only linker DNA. These results establish that the cassette encoding Cry2Ab is intact. No partial cassettes derived from that encoding Cry2Ab were detected.

The blot used above was stripped and re-probed with the full length enhanced CaMV 35S promoter. The DP50 long run did not produce any detectable background bands. Plasmid PV-GHBK11 mixed with DP50 in the short run produced the expected size bands at 5.5 and 3.2 Kb with no additional bands detectable. The DP50B long and short runs produced five bands at approximately 4.4, 5.3, 7.5, 9.4, and 22 Kb. Since these bands are present in both event MON15985 and the DP50B control they are considered background bands associated with the MON531 event. The MON 15985 long and short runs both produced one band at approximately 4.0 Kb which is not present in either the DP50 or the DP50B lanes. This corresponds to the fragment predicted for the cassette encoding Cry2Ab given the result obtained with the cry2Ab coding region probe. A second band in the MON15985 lanes resulting from hybridization to the enhanced CaMV 35S promoter associated with the cassette encoding UidA (GUS) is predicted but not apparent in the test lanes. The results of the NOS 3' polyadenylation sequence probe, discussed below, demonstrate that the enhanced CaMV 35S promoter sequence associated with the UidA encoding cassette is present, but the 4.4 Kb band co-migrates with a 4.4 Kb background band and is not apparent. No extraneous promoters were detected.

The blot used above was re-stripped and re-probed with the full length NOS 3' polyadenylation sequence. The DP50 long run did not produce any detectable background bands. Plasmid PV-GHBK11 mixed with DP50 short run produced the expected size bands at 5.5 and 3.2 is Kb with no additional bands detectable. The DP50B long and short runs produced one band at approximately 1.2 Kb. Since this band is present in both event MON15985 and the DP50B control it is considered background associated with the MON531 event. The MON15985 long and short runs each produced two bands which are not present in the DP50 or the DP50B lanes at approximately 4.0 and 4.4 Kb. The 4.0 Kb band corresponds to the fragment predicted for the cassette encoding Cry2Ab, given the result from above. The 4.4 Kb band was not apparent on the blot probed with the enhanced CaMV 35 S promoter because it co-migrates with the 4.4 Kb background band seen on that blot. This segment is associated with the uidA cassette.

These results establish that the Cry2Ab encoding cassette is intact and that there is a 66 bp deletion between the BamHI site and the 3' end of the transformation cassette, which does not include any of the NOS 3' polyadenylation sequence at the 3' end of the cassette encoding Cry2Ab. No partial cassettes derived from that encoding Cry2Ab were detected.

Genomic DNA isolated from MON15985, DP50B, DP50 (non-transgenic control) and DP50 mixed with plasmid PV-GHBK11 DNA was digested with EcoRI and BglII to release the entire uidA coding region. The blot was probed with the full-length uidA coding region. The DP50 non-transgenic control long run and the DP50B control long and short runs showed no detectable hybridization bands. Plasmid PV-GHBK11 mixed with DP50 short run produced the expected ~1.9 Kb band which corresponds to the entire uidA coding region. Both the long and short runs of event MON15985 DNA also produced a 1.9 Kb band which corresponds to the expected size of an intact uidA coding region. This result establishes that event MON15985 contains the intact uidA coding region, with no additional fragments detected.

DNA from the test and control substances was digested with BamHI and SphI to release the entire uidA cassette (i.e. uidA coding region, the enhanced CaMV 35S promoter, and the NOS 3' polyadenylation sequence). The plasmid PV-GHBK11 was digested with PstI and spiked into the DP50 short run samples after digestion (except for the NOS 3' polyadenylation sequence probe blot in which the plasmid was digested with BamHI and SphI). This was done to show the size of an intact full-length uidA cassette.

The blot was probed with the full length uidA coding region. As expected, the DP50 non-transgenic control long run and the DP50B control long and short runs showed no detectable hybridization bands. Plasmid PV-GHBK11 mixed with DP50 short run produced the expected 2.8 Kb band which corresponds to the entire uidA cassette. Both the MON15985 long and short runs produced an approximately 2.5 Kb band. This result indicates that a portion of the uidA cassette was not present. The 5' insert-to-plant junction, previously determined by genome walking, was verified by PCR analysis. It had been demonstrated previously that 284 bp of the 5' portion of the transformation cassette were deleted. These results establish that the uidA cassette is missing approximately 260 bp of the 5' promoter sequence and 24 bp of polylinker DNA derived from the multiple cloning site of the plasmid. Odell et al. (1985) showed that such a deletion should not affect accurate transcription initiation. No additional partial uidA cassettes were detected with the uidA coding region probe.

The blot used above was stripped and re-probed with the full length enhanced CaMV 35S promoter. The DP50 long run did not produce any background bands. Plasmid PV-GHBK11 mixed with DP50 short run produced the expected size bands at 1.5 and 2.8 Kb with no additional bands detected. The DP50B long and short runs produced five bands at approximately 4.3, 4.6, 5.0, 6.6, and 8.5 Kb. Since these bands are present in both event MON15985 and the DP50B control they are considered background bands associated with the MON531 event. The MON15985 long and short runs each produced two bands at approximately 2.5 and 1.0 Kb not present in the DP50 or the DP50B lanes. The 2.5 Kb band corresponds to the fragment predicted for the uidA cassette. The 1.0 Kb band results from the enhanced CaMV 35S promoter associated with the cassette encoding Cry2Ab. No extraneous promoters were detected.

The blot was probed with the full length NOS 3' polyadenylation sequence. The DP50 long run did not produce any detectable background bands. Plasmid PV-GHBK11 mixed with DP50 short run produced the expected size bands at 3.8 and 2.2 Kb with no additional bands detected. The DP50B long and short run produced one band at approximately 1.2 Kb. Since this band is present in both event 15985 and the DP50B control it is considered background associated with the MON531 event. The MON15985 long and short runs each produced two bands not present in the DP50 or the DP50B lanes at approximately 2.5 and 2.3 Kb. The 2.5 Kb band corresponds to the fragment predicted for the uidA cassette. The 2.3 Kb band results from NOS 3' polyadenylation sequence associated with the cassette encoding Cry2Ab.

These results confirm that the uidA cassette is missing approximately 260 bp of the 5' end of the enhanced CaMV 35S promoter but is otherwise intact.

Genomic DNA isolated from event MON15985, DP50B, DP50 (non-transgenic control) and DP50 mixed with plasmid PV-GHBK11 DNA was digested with KpnI. The blot was probed with the entire backbone sequence. The DP50 long run showed no detectable hybridization bands. Plasmid PV-GHBK11 mixed with DP50 DNA produced one band at the expected size of 2.6 Kb for the entire backbone. The DP50B long and short run produced a single band at approximately 22 Kb. Since this band is present in both event MON15985 and the DP50B control it is considered background associated with the MON531 event. The MON15985 long and short runs contained the 22 Kb background band with no additional hybridization. This result establishes that event MON15985 does not contain any detectable plasmid backbone sequence.

PCR was performed on genomic DNA to confirm the insert-to-plant junction sequences at the 5' and 3' ends of the MON15985 insert. As expected, the non-transgenic samples did not yield a PCR product when either the 5' or 3' primer set was used. The DP50B sample used as the control did not yield products with either primer pair, as expected. A different event prepared using the same construct and selected for expression of Cry2Ab, MON15813, also did not yield products when either primer set was used. The MON15985 genomic DNA yielded the correct size products when 5' end using primer pairs and 3' end primer pairs. This PCR analysis confirmed the 5' and 3' border sequences of MON15985.

The insect protected cotton event MON15985 was produced by particle acceleration technology using a KpnI DNA segment containing a cassette encoding Cry2Ab and UidA. The MON15985 event contains a single DNA insert located on a 9.3 Kb ScaI fragment. This insert contains one complete copy of the inserted cassette which is missing approximately 260 bp at the 5' end of the enhanced CaMV 35S promoter driving expression of the UidA coding sequence. PCR was used to verify the 5' and 3' junction sequences of the insert with the plant genome, as well as the intactness of the 5' and 3' ends of the insert. Event MON15985 does not contain any detectable plasmid backbone sequence resulting from the transformation event. Based on the enzymes used in this study, the restriction pattern of the cry1Ac insert is not changed by the insertion of the DNA inserted comprising the cry2Ab coding sequence.

Thus, SEQ ID NO:14, SEQ ID NO:15, SEQ ID NO:16, SEQ ID NO:17, and SEQ ID NO:18 and sequences comprising these sequences, are diagnostic for the insertion which gave rise to cotton event MON15985. With reference to FIG. 1, these sequences are reference numbers 2, 4, 6, 9, and 11 respectively.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

The invention claimed is:

1. An insect resistant cotton plant, seed of said cotton plant having been deposited with the American Type Culture Collection under accession number PTA-2516.

2. An insect resistant cotton plant, comprising incorporated into the plant's genome an insert DNA encoding Cry2Ab and DNA having nucleotide sequences of SEQ ID NO:14, SEQ ID NO:15, SEQ ID NO:16, SEQ ID NO:17 and SEQ ID NO:18.

3. A progeny plant of the cotton plant of claim 1 or 2, wherein DNA of said progeny plant is capable of producing at least one amplicon of approximately 1.5 kb using primers having the sequences of SEQ ID NO:34 and SEQ ID NO:36.

4. An insect resistant cotton plant, wherein DNA encoding Cry2Ab and DNA having nucleotide sequences of SEQ ID NO:11 and SEQ ID NO:12 form a part of the plant's genome.

5. The insect resistant cotton plant of claim 2, wherein the genomic DNA of said cotton plant is capable of producing at least one amplicon of approximately 1.5 kb using primers having the sequences of SEQ ID NO: 34 and SEQ ID NO:36.

6. The insect resistant cotton plant of claim 2, wherein the cotton plant is heterozygous for the Cry2Ab insert.

7. The insect resistant cotton plant of claim 2, wherein the cotton plant is homozygous of the Cry2Ab insert.

8. A transgenic seed of the plant of claim 1, 2 or 3.

9. A transgenic seed of the plant of claim 2, wherein said seed comprises said nucleotide sequences.

10. A transgenic seed of the plant of claim 3, wherein said seed is capable of producing said amplicon.

11. A method of producing an insect resistant cotton plant comprising crossing the plant of claim 1, 2 or 3 with another cotton plant, and selecting insect resistant progeny by analyzing for at least one nucleotide sequence selected from the group consisting of SEQ ID NO:14, SEQ ID NO:15, SEQ ID NO:16, SEQ ID NO:17 and SEQ ID NO:18.

12. A method of producing an insect resistant cotton plant comprising crossing the plant of claim 3 with another cotton plant, and selecting insect resistant progeny by analyzing for at least one nucleotide sequence selected from the group consisting of SEQ ID NO:14, SEQ ID NO:15, SEQ ID NO:16, SEQ ID NO:17 and SEQ ID NO:18.

* * * * *

UNITED STATES PATENT AND TRADEMARK OFFICE
CERTIFICATE OF CORRECTION

PATENT NO. : 7,223,907 B2 Page 1 of 1
APPLICATION NO. : 10/480223
DATED : May 29, 2007
INVENTOR(S) : Scott A. Huber et al.

It is certified that error appears in the above-identified patent and that said Letters Patent is hereby corrected as shown below:

Claim 8, column 48, line 40, delete "2 or 3".

Claim 11, column 48, line 46, delete "1, 2 or 3" and insert -- 1 or 2 --.

Signed and Sealed this

Thirty-first Day of July, 2007

JON W. DUDAS
*Director of the United States Patent and Trademark Office*